(12) United States Patent
Baxter, III et al.

(10) Patent No.: US 10,172,609 B2
(45) Date of Patent: Jan. 8, 2019

(54) SUTURING INSTRUMENT WITH LOCKING ARTICULATION KNOB

(71) Applicant: Ethicon Endo-Surgery, LLC, Guaynabo, PR (US)

(72) Inventors: Chester O. Baxter, III, Loveland, OH (US); Daniel L. Geiger, Ft. Thomas, KY (US)

(73) Assignee: Ethicon LLC, Guaynabo, PR (US)

( * ) Notice: Subject to any disclaimer, the term of this patent is extended or adjusted under 35 U.S.C. 154(b) by 396 days.

(21) Appl. No.: 14/918,906

(22) Filed: Oct. 21, 2015

(65) Prior Publication Data
US 2017/0112488 A1    Apr. 27, 2017

(51) Int. Cl.
*A61B 17/04* (2006.01)
*A61B 17/06* (2006.01)

(52) U.S. Cl.
CPC .......... *A61B 17/0469* (2013.01); *A61B 17/06* (2013.01); *A61B 2017/047* (2013.01)

(58) Field of Classification Search
CPC .......... A61B 17/0469; A61B 17/06133; A61B 2017/00367; A61B 2017/00407; A61B 2017/00473; A61B 2017/0608; A61B 2017/2927; A61B 2090/0811; A61B 17/2909; A61M 25/0136; A61M 25/0105
See application file for complete search history.

(56) References Cited

U.S. PATENT DOCUMENTS

| | | | |
|---|---|---|---|
| 8,702,732 B2 | 4/2014 | Woodard et al. | |
| 9,168,037 B2 | 10/2015 | Woodard et al. | |
| 9,357,998 B2 | 6/2016 | Martin et al. | |
| 9,375,212 B2 | 6/2016 | Martin et al. | |
| 9,474,522 B2 | 10/2016 | Deck et al. | |
| 2007/0250113 A1* | 10/2007 | Hegeman | A61B 1/0055 606/207 |
| 2015/0351747 A1* | 12/2015 | Martin | A61B 17/0469 606/145 |
| 2016/0367238 A1* | 12/2016 | Deck | A61B 17/0469 |
| 2016/0367243 A1 | 12/2016 | Martin et al. | |

* cited by examiner

*Primary Examiner* — Jonathan Miles
*Assistant Examiner* — George J Ulsh
(74) *Attorney, Agent, or Firm* — Frost Brown Todd LLC

(57) ABSTRACT

A surgical instrument for treating a patient includes a shaft assembly and a body assembly. The shaft assembly includes an articulation joint that is operable to selectively articulate a distal end portion relative to a proximal end portion. The body assembly includes a joint drive assembly, an actuator, and a clutch lock mechanism. The clutch lock mechanism is operatively connected between the actuator and the joint drive assembly. The actuator is configured to actuate the clutch lock mechanism from a locked state to an unlocked state. In the locked state, the clutch lock mechanism is configured to seize the joint drive assembly and inhibit movement of the articulation joint. In the unlocked state, the clutch lock mechanism is configured to transmit movement of the actuator to the joint drive assembly for moving the distal end portion of the shaft assembly.

20 Claims, 22 Drawing Sheets

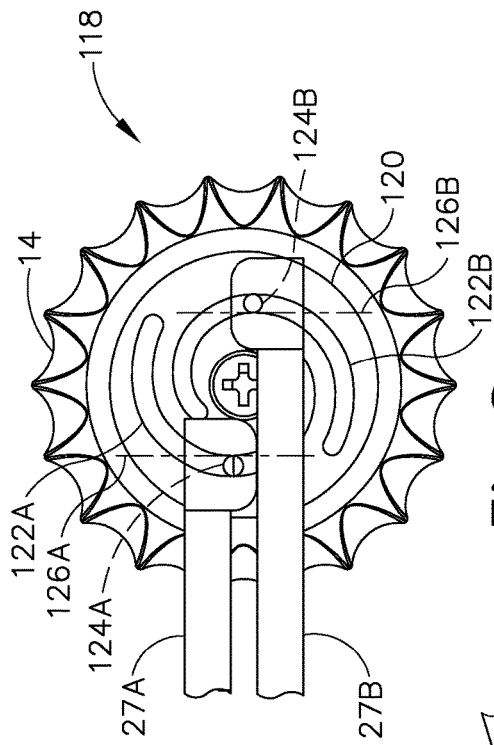
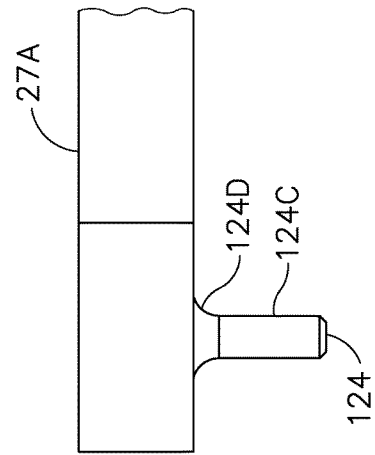
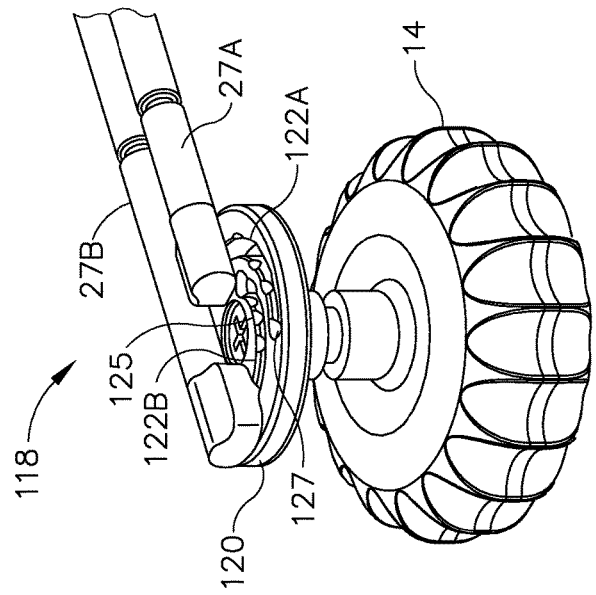

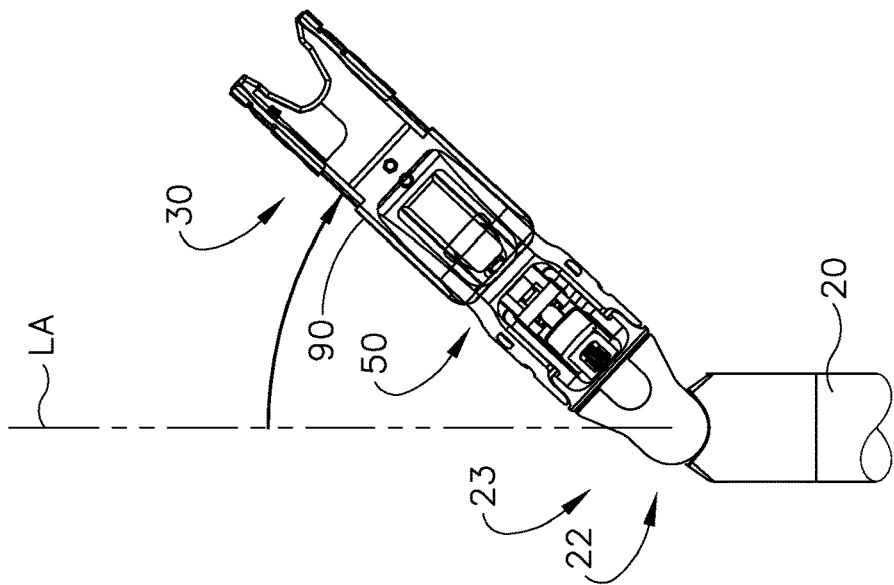
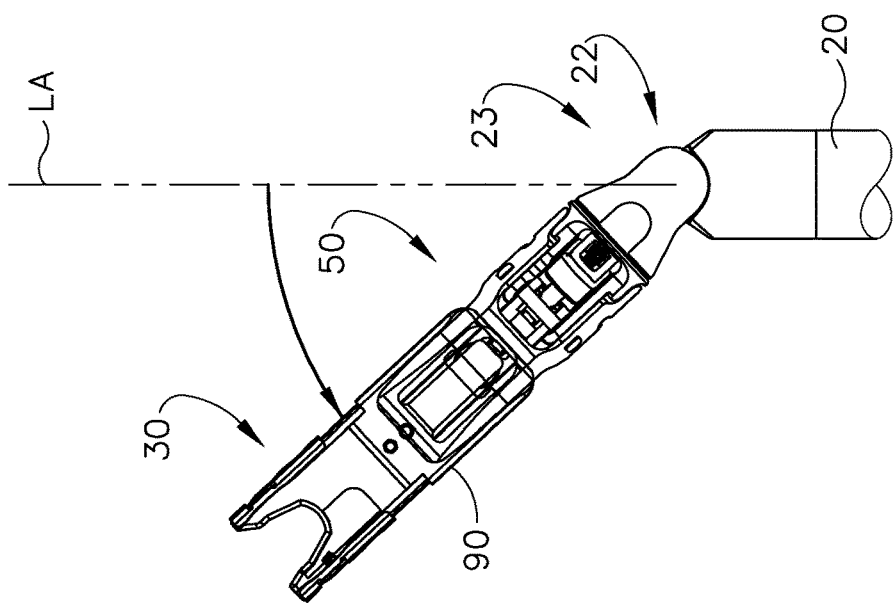
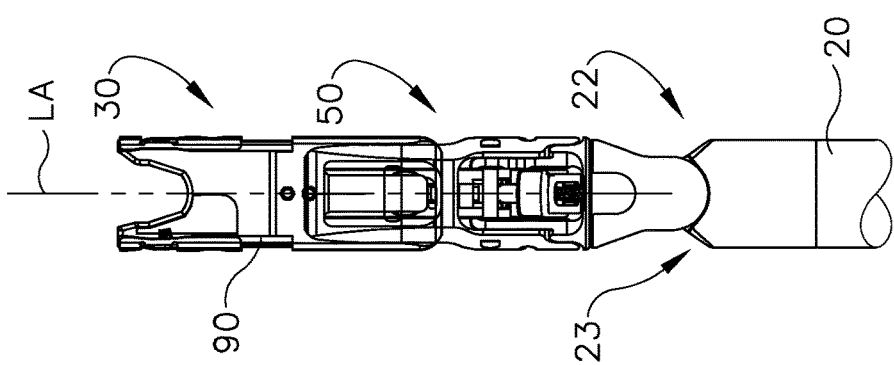

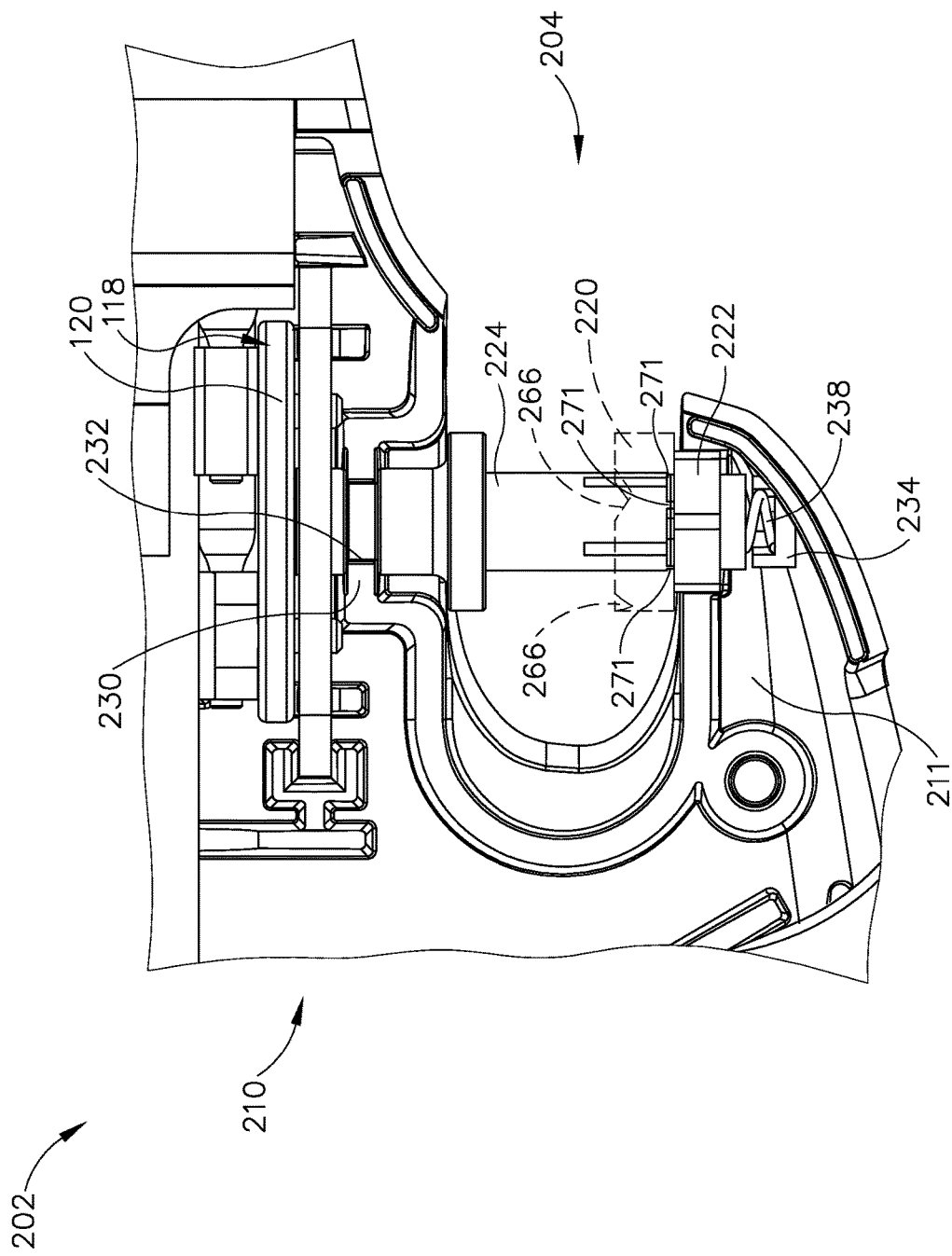

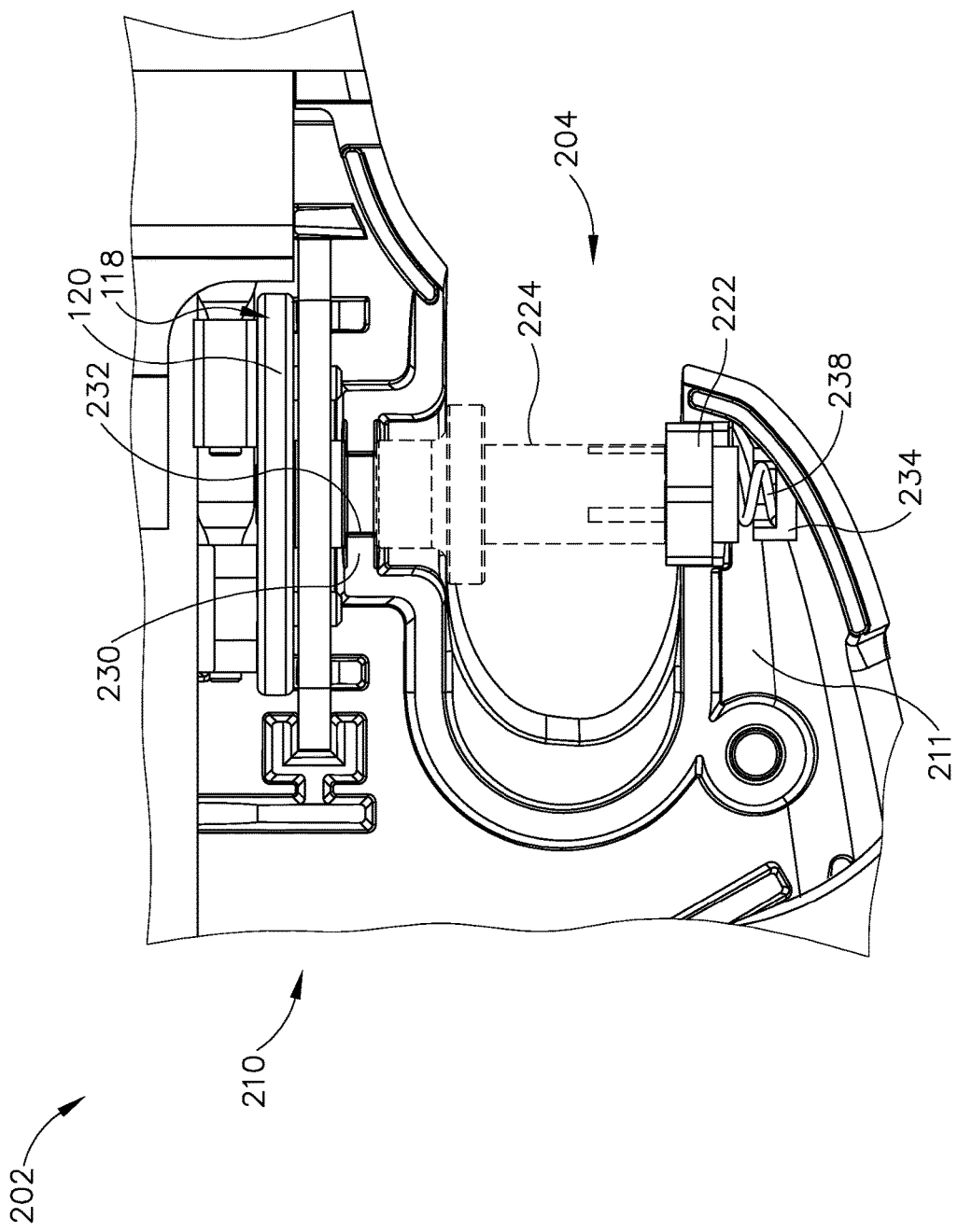

SUTURING INSTRUMENT WITH LOCKING ARTICULATION KNOB

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, now U.S. Pat. No. 9,168,037, issued Oct. 27, 2015, the disclosure of which is incorporated by reference herein; U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; and U.S. patent application Ser. No. 14/297,993, entitled "Jawed Cartridge receiving assembly for Needle Cartridge," filed Jun. 6, 2014, now U.S. Pat. No. 9,474,522, issued Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts a top plan view of an articulation control assembly of the handle assembly of FIG. 7;

FIG. 9 depicts a perspective view of the articulation control assembly of FIG. 8;

FIG. 10 depicts a side elevational view of an articulation rod and follower of the articulation control assembly of FIG. 8;

FIG. 11A depicts a top plan view of the cartridge receiving assembly of FIG. 2A, the cartridge of FIG. 3A, and the shaft assembly of the instrument of FIG. 1, with the cartridge receiving assembly aligned with the longitudinal axis of the shaft assembly;

FIG. 11B depicts a top plan view of the cartridge receiving assembly of FIG. 2A, the cartridge of FIG. 3A, and the shaft assembly of the instrument of FIG. 1, with the cartridge receiving assembly deflected in a first direction away from the longitudinal axis of the shaft assembly by the articulation control assembly of FIG. 8; and FIG. 11C depicts a top plan view of the cartridge receiving assembly of FIG. 2A, the cartridge of FIG. 3A, and the shaft assembly of the instrument of FIG. 1, with the cartridge receiving assembly deflected in a second direction away from the longitudinal axis of the shaft assembly by the articulation control assembly of FIG. 8;

FIG. 24E depicts a side elevational view of the articulation control assembly of FIG. 14, with the rotary knob of FIG. 15 removed for clarity, and with the transfer shaft aligned with the lock ring depressed in the unlocked position after a desirable rotation of the rotary knob;

FIG. 24G depicts a side elevational view of the articulation control assembly of FIG. 14, with the rotary knob of FIG. 15 removed for clarity, and with the lock ring released to the locked position against the transfer shaft after the desirable rotation of the rotary knob and the cam follower ring.

Figure 1:
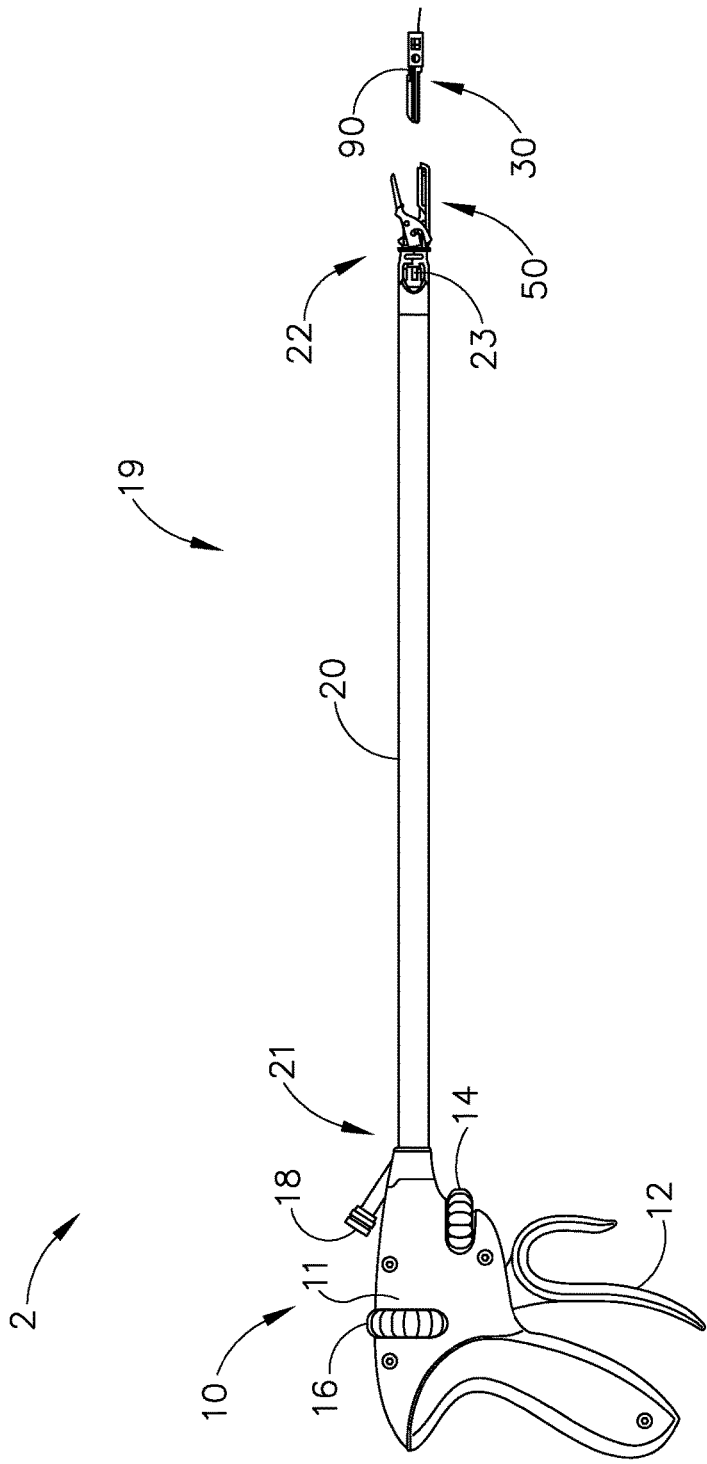
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal", "distal", "upper", and "lower" are defined herein relative to an operator or other operator grasping a surgical instrument having a distal surgical end effector. The term "proximal" refers the position of an element closer to the operator or other operator, and the term "distal" refers to the position of an element closer to the surgical end effector of the surgical instrument and further away from the operator or other operator. The term "upper" refers to the position of the element closer to a top of the surgical instrument when viewed by the user from above, and the term "lower" refers to the position of the element closer to a bottom of the surgical instrument when viewed by the user from below. As such, proximal and distal portions are generally in longitudinal opposition as described herein, whereas upper and lower portions are generally in transverse opposition as described herein.

I. Overview of Exemplary Surgical Suturing Instrument

FIG. 1 illustrates an example of a surgical suturing instrument (2). Instrument (2) comprises a handle assembly (10) and a shaft assembly (19) having an elongate shaft (20) extending from a distal end portion (22) to a proximal end portion (21) thereof. Distal end portion (22) includes a cartridge receiving assembly (50), which is operable to receive a needle applier cartridge (30). Shaft (20) defines a longitudinal axis extending from proximal end portion (21) to distal end portion (22). Handle assembly (10) is connected to proximal end portion (21) of shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to distal end portion (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first user input member (12), shown here as a trigger that pivots between opened and closed positions, may be used to selectively actuate needle applier cartridge (30). The trigger may be spring biased to return the trigger to its open position. A second user input member (14), shown here as a rotary knob, may be used to selectively articulate shaft (20). A third user input member (16), shown here as a rotary knob, may be used to selectively rotate needle applier cartridge (30) about shaft (20). Of course, the number, type, configuration, and operation of input members (12, 14, 16) may vary.

Figure 2A:
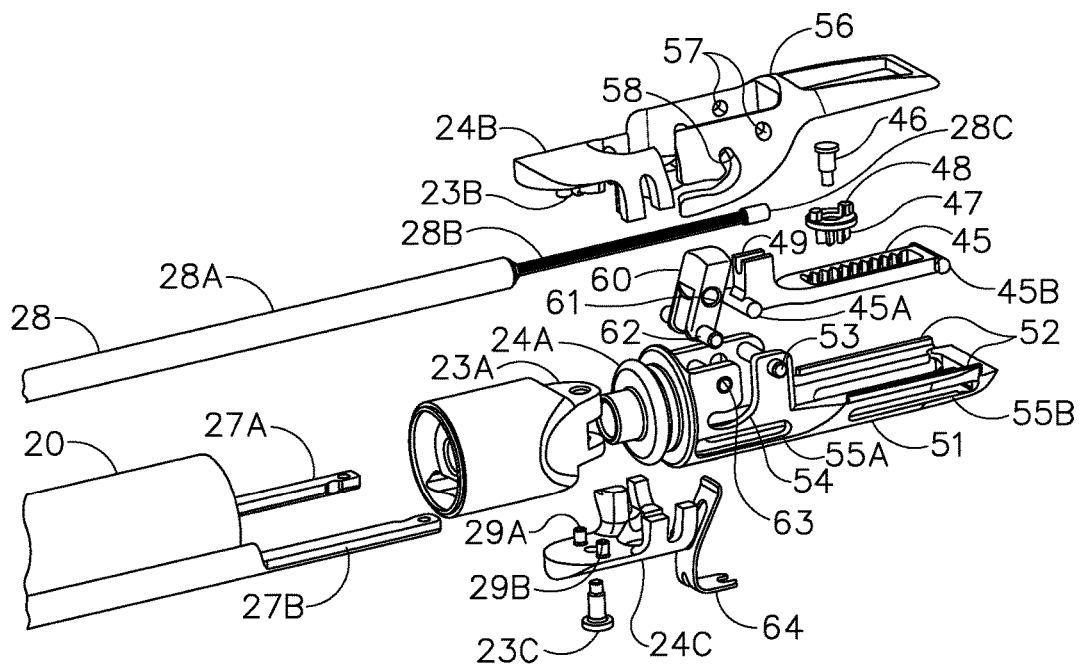
FIG. 2A depicts top perspective exploded view of a cartridge receiving assembly of the instrument of FIG. 1.
Figure 2B:
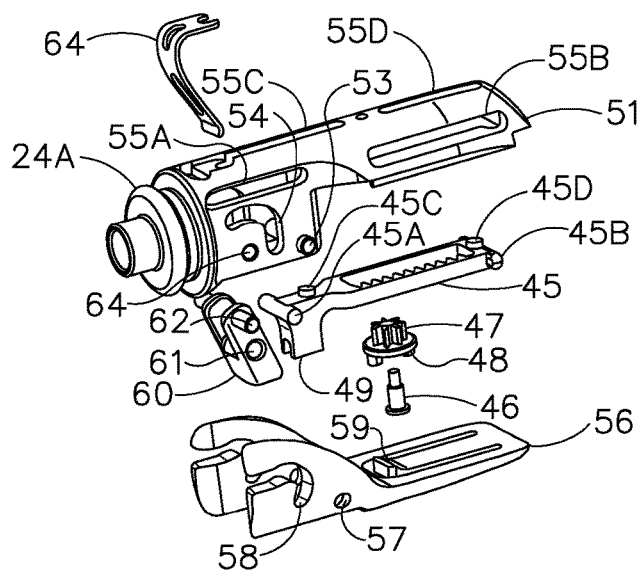
FIG. 2B depicts bottom perspective exploded view of the cartridge receiving assembly of FIG. 2A.

FIGS. 2A-2B illustrate exploded views of cartridge receiving assembly (50) of the present example. Distal end portion (22) of shaft (20) comprises an articulation joint (23) and a rotational bearing (24). Articulation joint (23) includes a knuckle (23A) that receives pins (23B, 23C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, rotary knob (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, 29B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by a pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first user input member (12) and to third user input member (16). Actuation of first user input member (12) will impart axial push and pull loads on drive rod (28) to longitudinally reciprocate rack (45) and thereby actuate needle applier cartridge (30). Actuation of third user input member (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received in hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
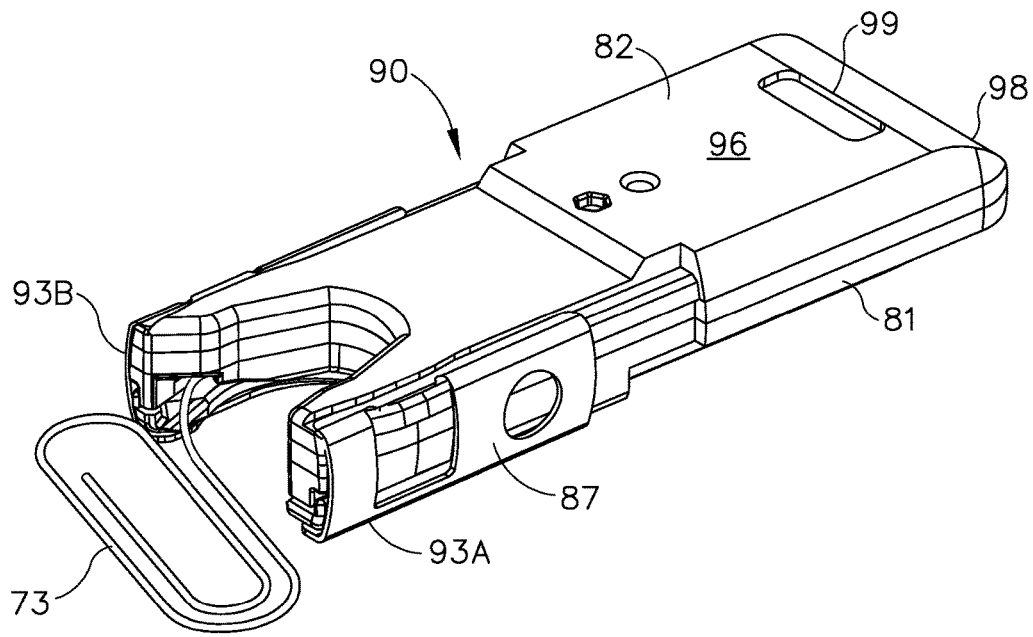
FIG. 3A depicts a top perspective view of an exemplary cartridge configured for receipt in the cartridge receiving assembly of FIG. 2A.
Figure 3B:
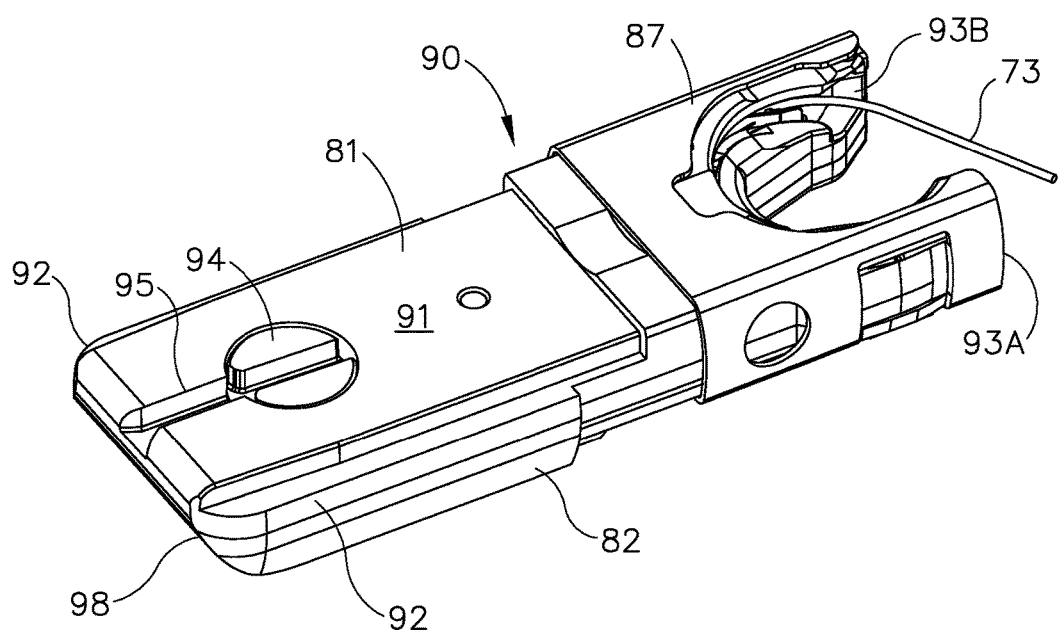
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) is adapted to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
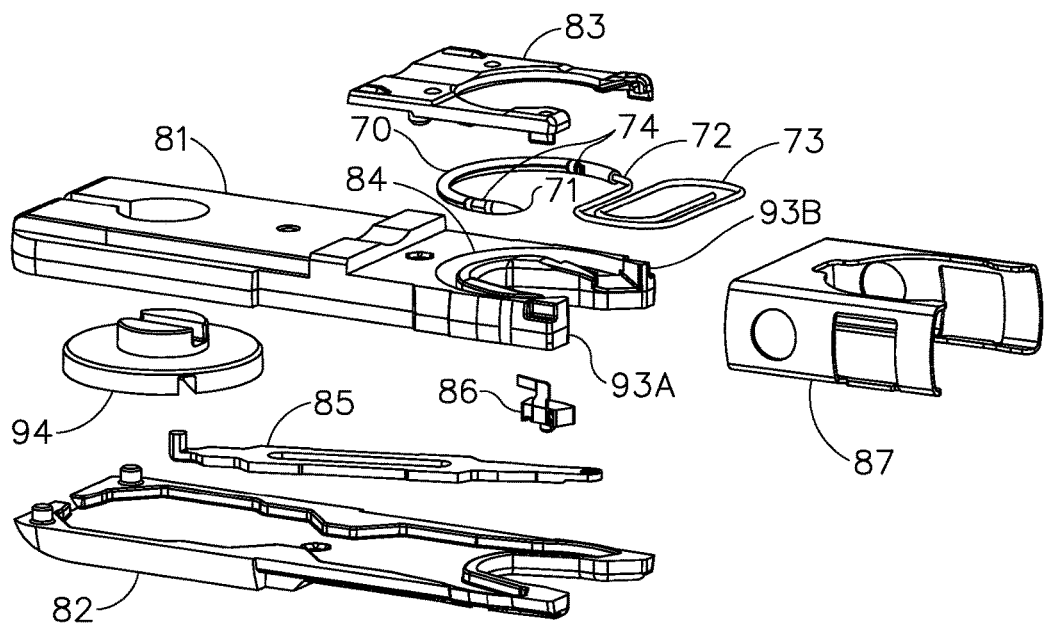
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from a trailing end (72) thereof. Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
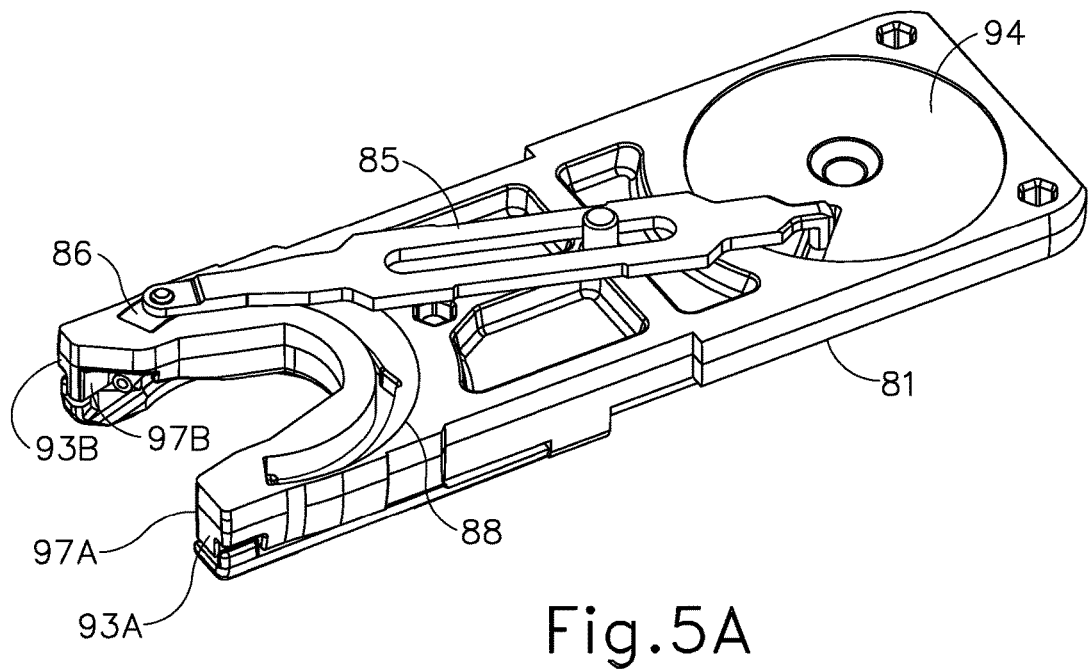
FIG. 5A depicts a perspective view of a drive assembly of the cartridge of FIG. 3A, with the drive assembly at one end of its stroke.
Figure 5B:
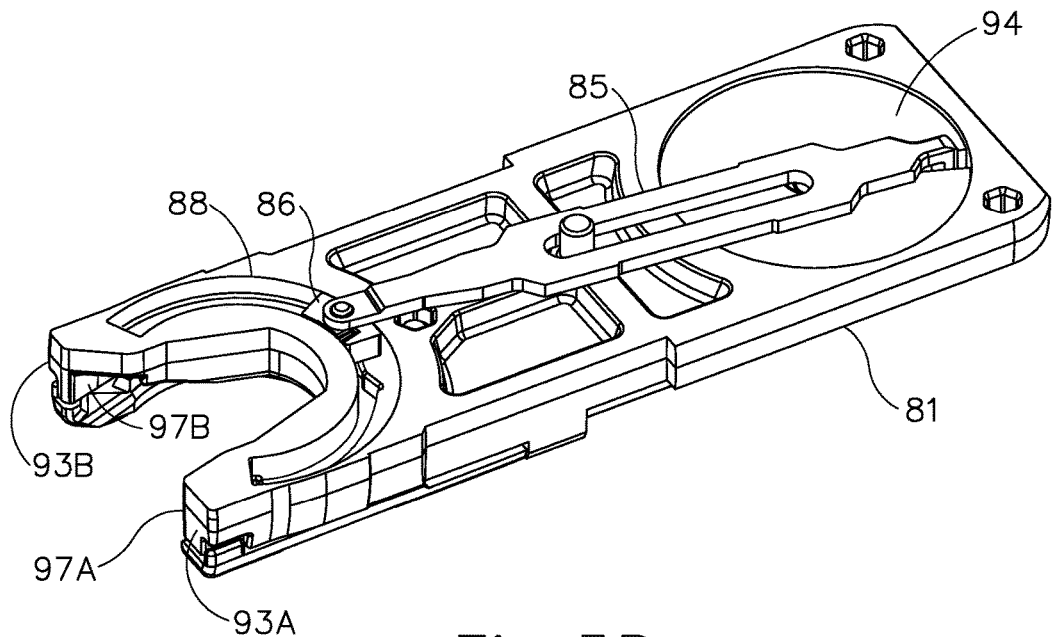
FIG. 5B depicts a perspective view of the drive assembly of FIG. 5A, with the drive assembly at mid-stroke.
Figure 5C:
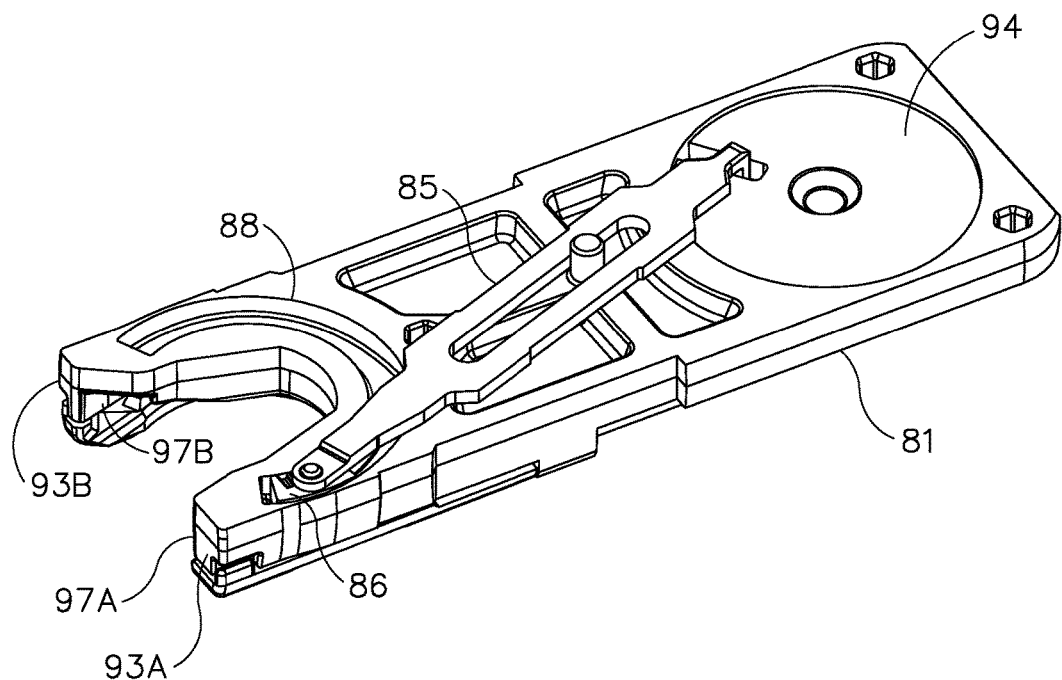
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) are omitted from FIGS. 5B-5C for clarity. Needle driver (86) rides in a carrier track (88) and extends into needle track (84) (see FIG. 4) to engage and drive needle (70). Link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
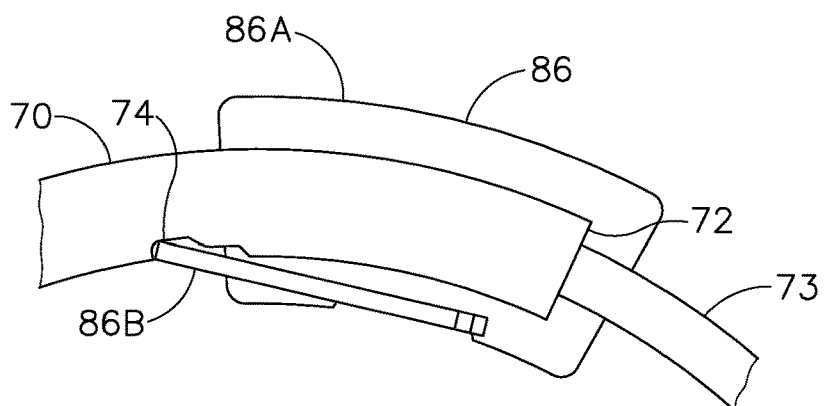
FIG. 6 depicts a partial plan view of a needle driver of the cartridge of FIG. 3A engaging a needle of the cartridge of FIG. 3A.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (86A) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C and FIG. 6, when first user input member (12) (see FIG. 1) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (97A) and entrance port (97B). Tissue interposed between arms (93A, 93B) will be pierced by leading end (71) of needle (70).

When first user input member (12) (see FIG. 1) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first user input member (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) (see FIG. 3A) will follow needle (70) and be threaded through the pierced tissue.

When first user input member (12) (see FIG. 1) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first user input member (12) being actuated twice. The sequence may be repeated as needed by the surgeon to achieve the desired suturing task.

Figure 7:
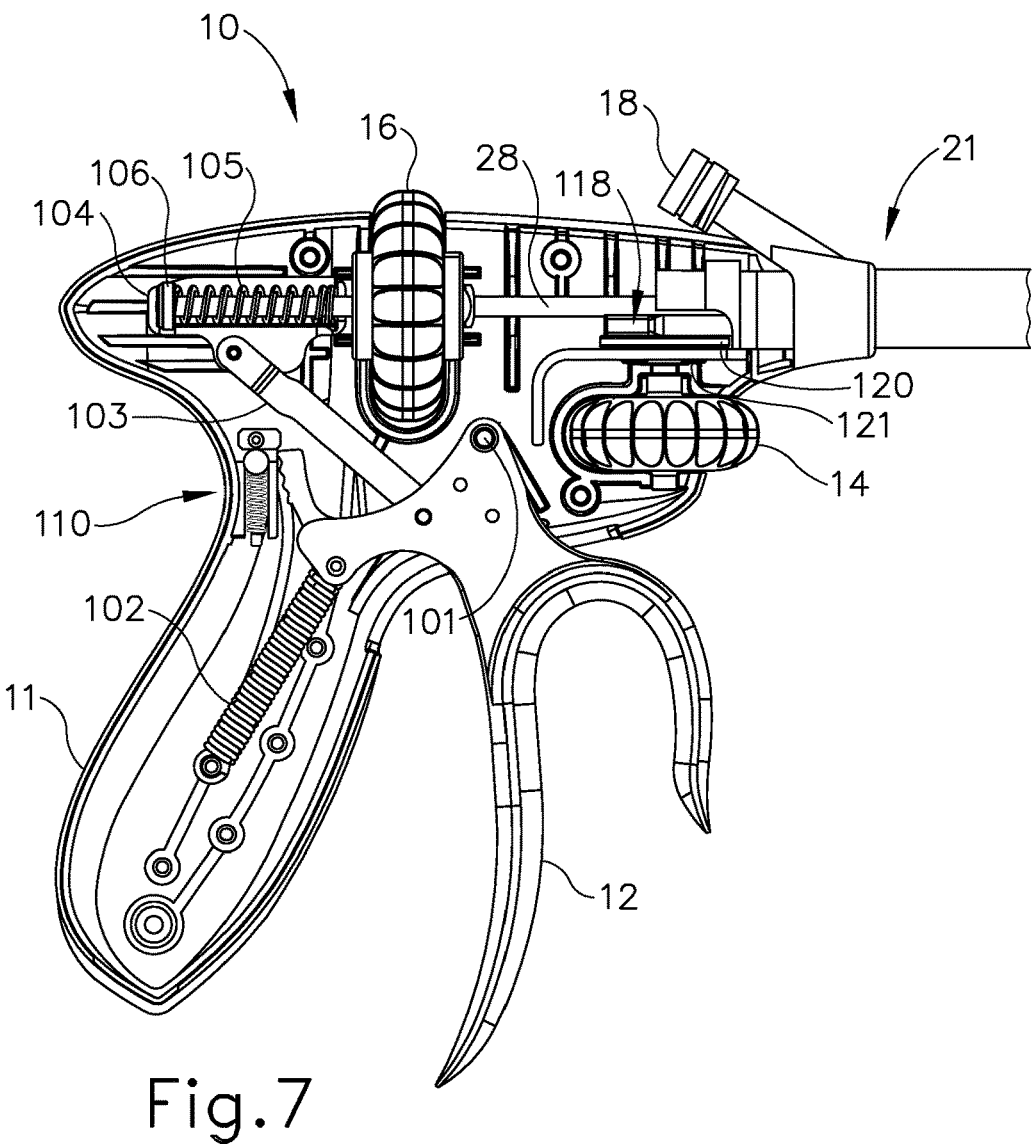
FIG. 7 depicts a side elevational view of the handle assembly of the instrument of FIG. 1, with a housing half removed to reveal internal components.

With respect to FIG. 1 and FIG. 7, rotary knob (14) is operable to selectively articulate joint (23) via a joint drive assembly (118). Rotary knob (14) rotates in a plane spaced below and generally parallel with shaft (20). Joint drive assembly (118) includes rods (27A, 27B) and a disk (120). An axle (121) connects rotary knob (14) to disk (120) in housing (11) that also rotates in a plane generally parallel with the shaft (20). As shown in FIG. 8, disk (120) comprises first and second cam slots (122A, 122B), each having a length with angular and radial components. In this embodiment, the cam slots (122A, 122B) are two identical spirals offset 180 degrees from one another. Each cam slot (122A, 122B) has an angular span between about 220 degrees and about 300 degrees, with their angular spans overlapping one another. Cam slots (122A, 122B) also increase their distance from the center of disk (120) in the same angular direction. Each cam slot (122A, 122B) has a radial span of about 0.100 inches and about 0.155 inches. Of course, the configuration and dimensions of cam slots (122A, 122B) may alternatively differ from the foregoing.

Cam slot (122A) receives a cam follower (124A) on a distal half of disk (120), and cam slot (122B) receives a cam follower (124B) on the proximal half of disk (120). Followers (124A, 124B) extend downwardly and generally normal from the proximal ends of rods (27A, 27B), respectively. In this example, followers (124A, 124B) are medially offset from longitudinal axes of the respective drive rod (27A, 27B). Rods (27A, 27B) are constrained to slide axially, so counterclockwise rotation of disk (120) moves rod (27B) proximally and simultaneously moves rod (27A) distally to articulate joint (23) to the left of the longitudinal axis (LA) of shaft (20), as shown in the transition from FIG. 11A to FIG. 11B. Similarly, clockwise rotation of disk (120) moves rod (27B) distally and simultaneously moves rod (27A) proximally, thereby articulating joint (23) to the right of the longitudinal axis (LA) of shaft (20), as shown in the transition from FIG. 11A to FIG. 11C.

With respect to FIG. 8 and FIG. 11A, cam slots (122A, 122B) each define a tangent axis (126A, 126B) where cam slot (122A, 122B) is engaged by the respective cam followers (124A, 124B). The tangent axes (126A, 126B) may be substantially normal to the longitudinal axes of rods (27A, 27B) so axial push and pull loads on rods (27A, 27B) introduced by side loads on cartridge receiving assembly (50) will not cause disk (120) to rotate. Accordingly, joint (23) will remain locked at its articulated angle. Frictional interfaces, detents, and other locking features, such as those discussed below, may be added to further prevent unintentional articulation.

FIG. 9 illustrates an alternative example of an articulation control. A plurality of detents (125) are positioned along cam slots (122A, 122B). In addition to preventing unintentional articulation, detents (125) may provide feedback to the surgeon indicating various angular positions of needle applier cartridge (30) relative shaft (20). Detents (125) may be indexed to correspond to one or more predetermined articulation angles, such as 0 degrees, 15 degrees, 45 degrees, and the like; or detents (125) may be equally distributed along cam slots (122A, 122B). Larger detents (127) may be located at the ends of the cam slots (122A, 122B).

Detents (125) open to the top surface of disk (120), but only partially extend into cam slots (122A, 122B). As shown in FIG. 10, follower (124) extends downwardly from articulation rod (27). Follower (124) includes a straight portion (124C) that closely fits in cam slots (122A, 122B) and a radius portion (124D) dimensioned to be received by detents (125). As disk (120) rotates, radius portion (124D) will raise and lower into detents (125) but the straight portion (124C) will follow and remain engaged in the cam slots (122A, B). In some versions, rod (27) will be biased downwardly toward disk (120) to provide a tactile and/or audible "click" as radius portion (124D) engages detents (125).

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, now U.S. Pat No. 9,474,522, issued Oct. 25, 2016, the disclosure of which is incorporated by reference herein; U.S. patent application Ser. No. 14/298,038, entitled "Circular Needle Applier with Cleats," filed Jan. 30, 2015, now U.S. Pat. No. 9,375,212, issued Jun. 28, 2016, the disclosure of which is incorporated by reference herein; and U.S. patent application Ser. No. 14/740,724, entitled "Suturing Instrument with Motorized Needle Drive," filed Jun. 16, 2015, now U.S. Pat. No. 9,888,914, issued Feb. 13, 2018, the disclosure of which is incorporated by reference herein. It should be understood that such details, explanations, examples, and alternative embodiments may be readily applied to the above-described instrument (10) and subcomponents thereof.

II. Exemplary Handle Assembly with Locking Articulation Joint

In some instances, it may be desirable to selectively lock articulation joint (23) in one of a plurality of positions in a way that secures cartridge receiving assembly (50) relative to a remainder of shaft assembly (19) and inhibits inadvertent movement of cartridge receiving assembly (50) at articulation joint (23) during use. For instance, in the event that the operator inadvertently bumps the cartridge receiving assembly (50) against another object, such as patient tissue or other surgical equipment, cartridge receiving assembly (50) will retain its desirable position (i.e., angular orientation) articulation joint (23). Articulation joint (23) may also automatically lock and unlock in one of the plurality of positions upon selective movement of rotary knob (14) for greater simplicity during a surgical procedure. Thus, selective movement of rotary knob (14) may simultaneously provide for both movement and selective locking and unlocking of articulation joint (23).

In the example shown in FIGS. 12-24E, a surgical suturing instrument (202) (see FIG. 12) includes a clutch lock mechanism (204) (see FIG. 13) that is operatively connected between a user input member, which is in the form of a rotary knob (214) (see FIG. 13), and joint drive assembly (118) that seizes movement of joint drive assembly (118) in order to lock articulation joint (23) in one of a plurality of articulation positions. In the present example, the plurality of positions is a plurality of predetermined discrete articulation positions. Various examples of how instrument (2) may be reconfigured to incorporate clutch lock mechanism (204) (see FIG. 13) will be described in greater detail below; while other examples will be apparent to those of ordinary skill in the art according to the teachings herein. It should be understood that the examples described below may function substantially similar to instrument (2) described above. In particular, instrument (202) described below may be used to suture tissue. To this end, like numbers referenced below indicate like features discussed above in greater detail.

Figure 12:
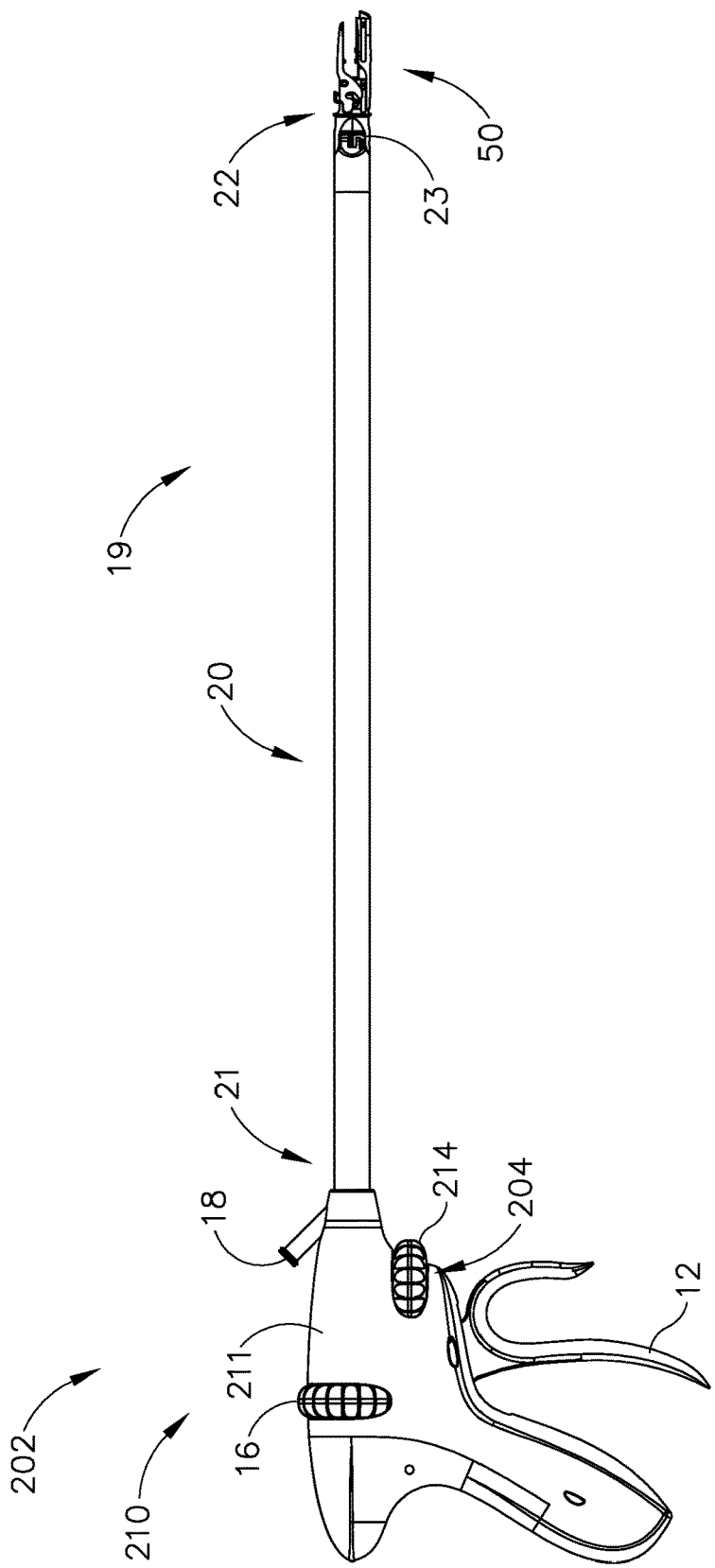
FIG. 12 depicts a side elevational view of another exemplary surgical suturing instrument.
Figure 13:
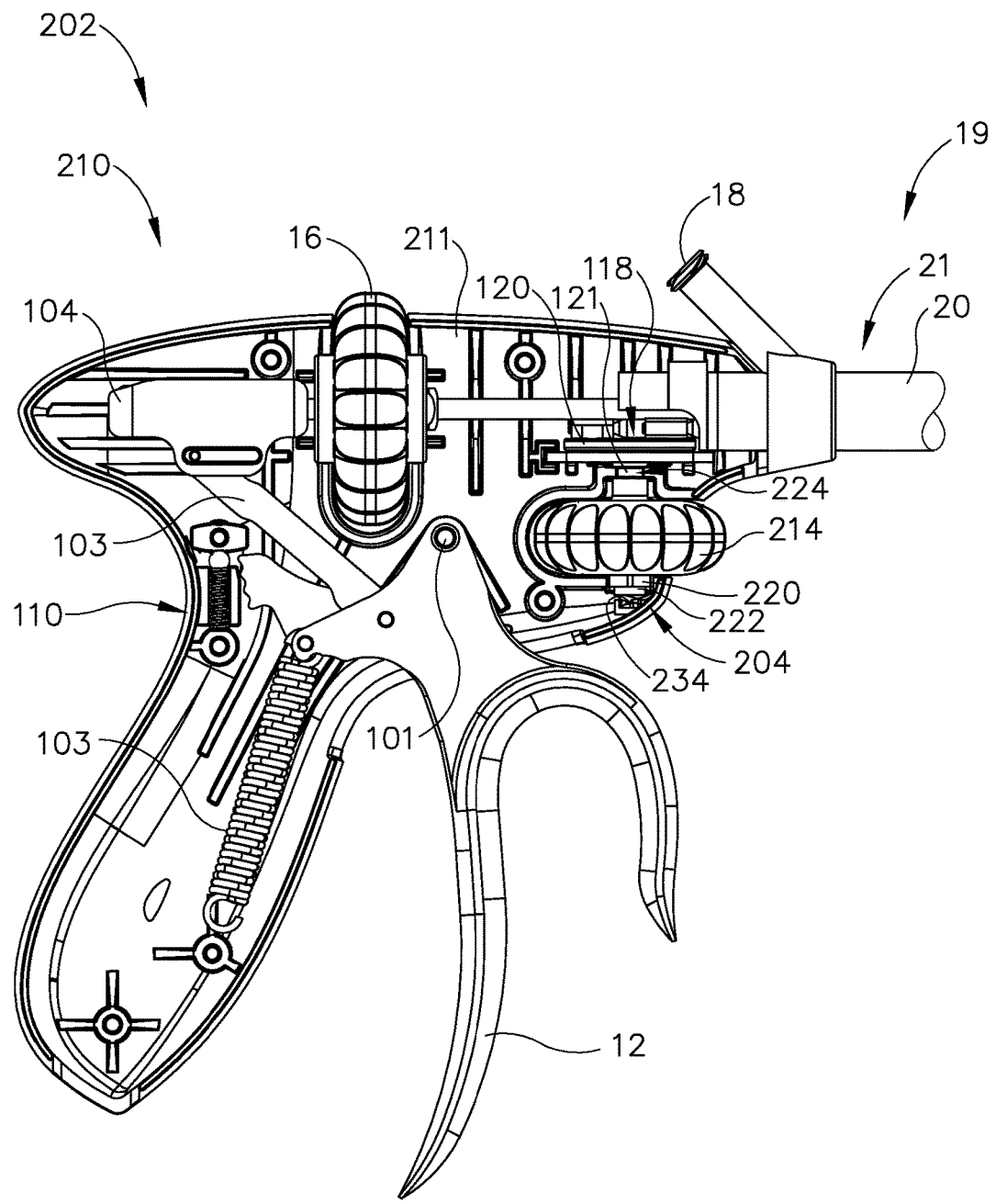
FIG. 13 depicts an enlarged side elevational view of the surgical suturing instrument of FIG. 12, with a housing half removed to reveal internal components.

As shown in FIGS. 12-13, instrument (202) of the present example a handle assembly (210) and shaft assembly (19). Handle assembly (210) is connected to proximal end portion (21) of shaft assembly (19). In this example, handle assembly (210) includes clutch lock mechanism (204) that is operatively connected between rotary knob (214) and joint drive assembly (118). As will be described in more detail below, clutch lock mechanism (204) generally secures articulation joint (23) in one of a plurality of articulation positions until the user selectively rotates rotary knob (214). Rotation of rotary knob (214) causes clutch lock mechanism (204) to transition from a locked state to an unlocked state, thereby transmitting further selective rotation of the rotary knob 214) to disk (120). Thus, joint drive assembly (118) is configured to articulate articulation joint (23) as discussed above; but clutch lock mechanism (204) in the locked state is configured to seize the joint drive assembly (118) when not being manipulated by the operator in order to prevent inadvertent movement of cartridge receiving assembly (50) at articulation joint (23).

It should be appreciated that handle assembly (210) may additionally include a variety of manual actuators including but not limited to a manual pistol grip handle, a scissor grip handle, a syringe grip handle, endoscopic rotary knobs, and the like. Handle assembly (210) could also take the form of a robotic interface, such as a DAVINCI puck, or a housing comprising gears or pulleys, servomechanisms, and the like. Thus, clutch lock mechanism (204) may be incorporated into a wide variety of handle assemblies for use with a wide variety of shaft assemblies generally contemplated herein. Handle assembly (210) and shaft assembly (19) are merely exemplary, and the invention is not intended to be unnecessarily limited to handle assembly (210) and shaft assembly (19) described herein.

Figure 14:
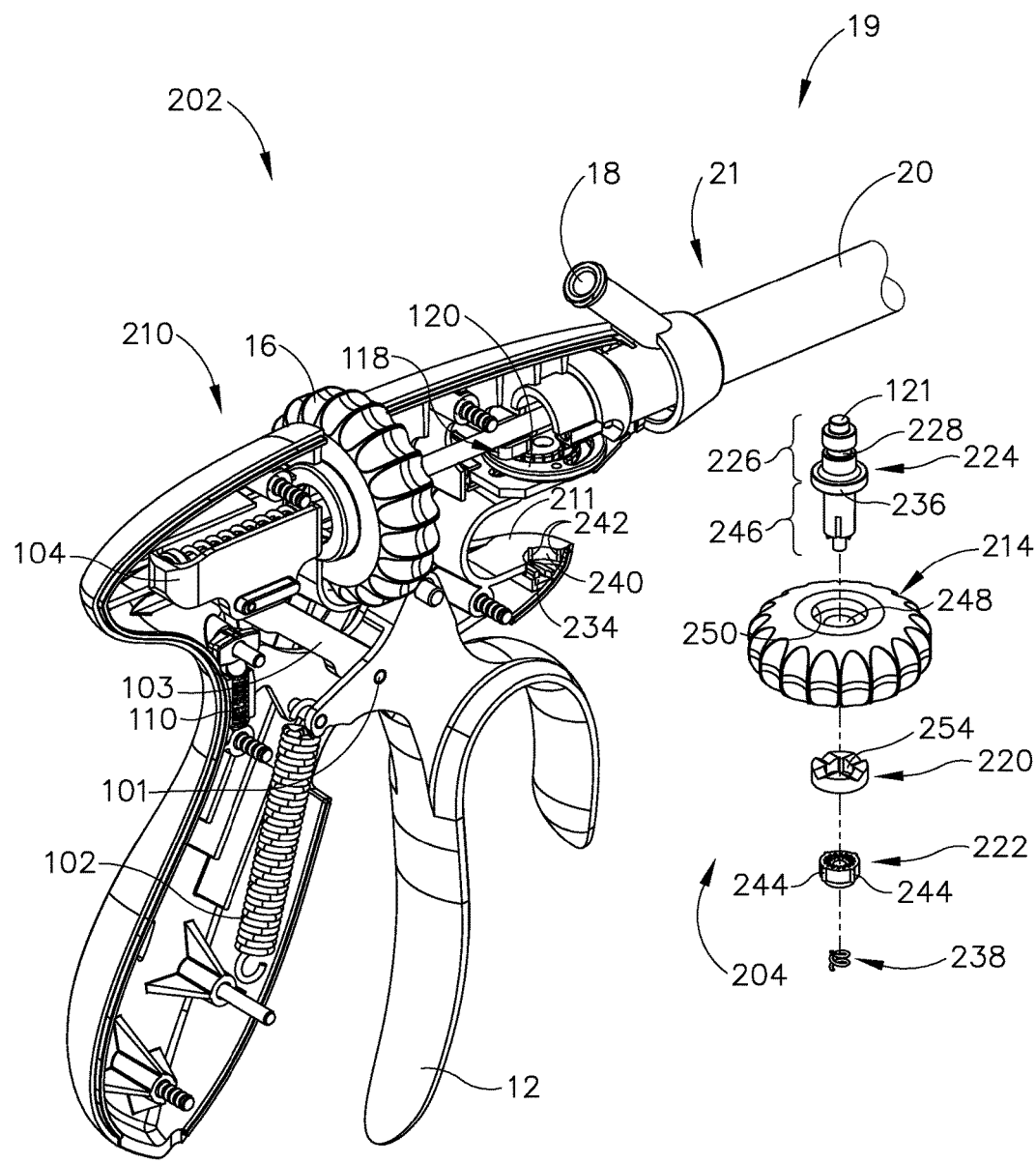
FIG. 14 depicts a partially exploded rear perspective view of the surgical suturing instrument of FIG. 13, with a housing half removed, and with components of an articulation control assembly exploded out.

Rotary knob (214) is configured to be manipulated by the operator for directing articulation of articulation joint (23) via clutch lock mechanism (204). As shown in FIGS. 13-14, clutch lock mechanism (204) of the present example includes a cam follower member in the form of a cam follower ring (220), a lock member in the form of a lock ring (222), and a transfer shaft (224), which includes axle (121) connected to disk (120). Transfer shaft (224) defines a longitudinal axis about which transfer shaft (224), cam follower ring (220), and rotary knob (214) are configured to rotate as mounted. Disk (120) is fixedly secured to axle (121) such that disk (120) will rotate unitarily with transfer shaft (224) about the longitudinal axis of transfer shaft (224). In the present example, an upper portion (226) of transfer shaft (224) includes axle (121), which has an upper annular groove (228). In the present example, the longitudinal axis of transfer shaft (224) is transverse to the longitudinal axis (LA) of shaft (20) and intersects the longitudinal axis (LA) of shaft (20). Alternatively, the longitudinal axis of transfer shaft (224) may be offset from the longitudinal axis (LA) of shaft (20), may be parallel to the longitudinal axis (LA) of shaft (20), and/or may have any other suitable relationship with the longitudinal axis (LA) of shaft (20).

Housing (211) includes an upper flange (230) (see FIG. 24A) defining an upper hole (232) (see FIG. 24A) that receives axle (121) such that upper flange (230) is received within upper annular groove (228). Upper flange (230) thereby rotatably supports transfer shaft (224) along the longitudinal axis of transfer shaft (224). While rotary knob (214), cam follower ring (220), lock ring (222), and transfer shaft (224) are generally cylindrical and/or ring-shaped, and are coaxially aligned along the longitudinal axis of transfer shaft (224), it will be appreciated that alternative arrangements and shapes of user input members, cam follower members, lock members, and transfer shafts may be used in accordance with the invention described herein. For example, an alternative user input member that is configured to translate, rotate, or any combination thereof under operator manipulation may engage an alternative clutch lock mechanism for articulating, locking, and unlocking articulation joint (23) (see FIG. 1). As such, it will be appreciated that alternative structures may form alternative clutch lock assemblies and the invention is not intended to be unnecessarily limited to the particular examples of rotary knob (214), cam follower ring (220), lock ring (222), and transfer shaft (224).

Housing (211) further includes a seat flange (234) that resiliently supports lock ring (222), cam follower ring (220), and rotary knob (214) upward against a stop flange (236) of transfer shaft (224). As such, rotary knob (214) is captured relative to housing (211) between cam follower ring (220) and stop flange (236) of transfer shaft (224) for selective rotation by the operator. More particularly, seat flange (236) directly supports a biasing element (238), such as a coil spring, with lock ring (222) resting directly thereon within a mount aperture (240) of housing (211). Mount aperture (240) is further defined by a plurality of transversely extending slots (242), which respectively receive a plurality of transversely extending ridges (244) angularly positioned about lock ring (222). Thereby, ridges (244) respectively cooperating within slots (242) prevent lock ring (222) from rotating, while also guiding lock ring (222) to slide transversely between locked and unlocked positions, which will be discussed below in greater detail. Upwardly biased lock ring (222) engages cam follower ring (220) and, in turn, sandwiches cam follower ring (220) against rotary knob (214) such that rotary knob (214) is resiliently supported against stop flange (236) of transfer shaft (224).

In order to consolidate clutch lock mechanism (204) as shown in FIG. 14 within housing (211), rotary knob (214), cam follower ring (220), and lower portion (246) of transfer shaft (224) are nested together and coaxially aligned. In one example, rotary knob (214) includes a knob bore (248), extending along the longitudinal axis of transfer shaft (224), that receives lower portion (246) of transfer shaft (224) through an upper opening (250) and receives cam follower ring (220) through a lower opening (252) (see FIG. 16). A cam follower bore (254) extending through cam follower ring (220), along the longitudinal axis of transfer shaft (224), also receives lower portion (246) of transfer shaft (224) within knob bore (248). As such, knob bore (248) receives both of transfer shaft (224) and cam follower ring (220) in order to reduce the overall dimensions of clutch lock mechanism (204).

Figure 15:
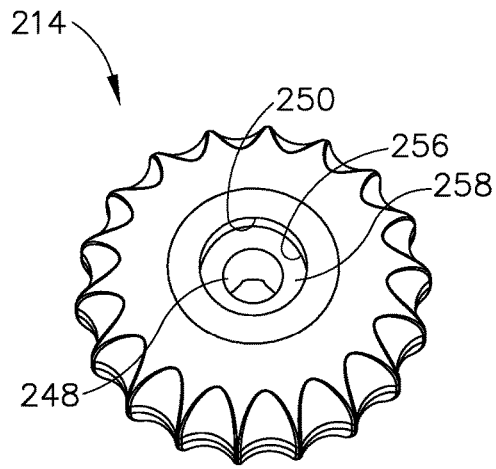
FIG. 15 depicts a top perspective view of a rotary knob of the articulation control assembly of FIG. 14.
Figure 16:
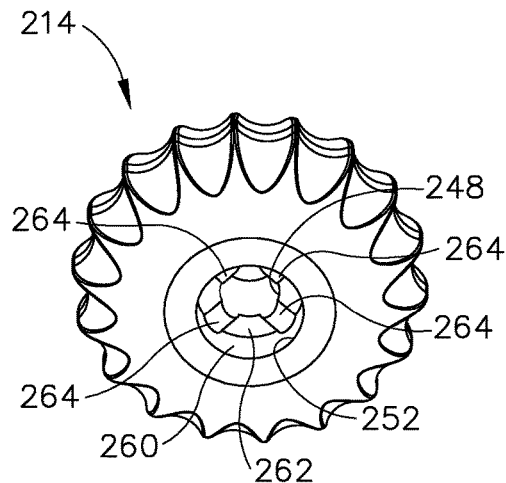
FIG. 16 depicts a bottom perspective view of the rotary knob of FIG. 15.
Figure 17:
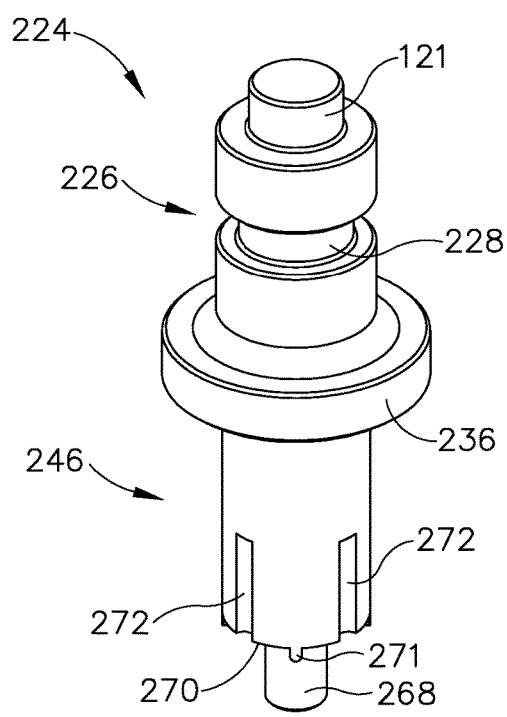
FIG. 17 depicts a top perspective view of a transfer shaft of the articulation control assembly of FIG. 14.

FIGS. 15-22 show rotary knob (214), transfer shaft (224), cam follower ring (220), and lock ring (222) in greater detail. With respect to rotary knob (214), FIGS. 15-16 show knob bore (248) extending along the longitudinal axis of transfer shaft (224) from upper and lower openings (250, 252), respectively. An upper annular groove (256) extends along the axis from upper opening (250) to an upper seat surface (258), which is configured to abut against stop flange (236) of transfer shaft (224) (see FIG. 18). In addition, a lower annular groove (260) extends along the longitudinal axis of transfer shaft (224), from lower opening (252) to a cam surface (262). Cam surface (262) includes a plurality of cam studs (264) extending downwardly to be received respectively within a plurality of cam slots (266) of cam follower ring (220) (see FIG. 19). As described in greater detail below, rotary knob (224) may rotate about the longitudinal axis of transfer shaft (224) during operation of joint drive assembly (118); but rotary knob (214) does not translate along the longitudinal axis of transfer shaft (224). It should be understood that rotary knob (214) is not fixedly secured to transfer shaft (224) in this example, such that rotary knob (214) and transfer shaft (224) do not rotate together unitarily. Instead, rotation of rotary knob (214) is communicated to transfer shaft (224) via cam follower ring (220), as will be described in greater detail below.

Transfer shaft (224) includes upper portion (226) and lower portion (246) as discussed above and shown in FIGS. 17-18. In addition, lower portion (246) includes a lower extension (268) projecting from a lower lock face (270), each of which is directed toward lock ring (222) (see FIG. 21). More particularly, lower extension (268) is generally cylindrical and extends along the longitudinal axis of transfer shaft (224); and is configured to be slidably received within lock ring (222) (see FIG. 21). Lower lock face (270) further includes a plurality of lock tabs (271) extending toward lock ring (222) (see FIG. 21) for releasable engagement with lock ring (222) in order to inhibit rotation of transfer shaft (224) as discussed below in greater detail. Similarly, lower portion (246) of transfer shaft (224) includes a plurality of longitudinally extending, inwardly directed slots (272) that are configured to engage cam follower ring (220) (see FIG. 19) to inhibit relative rotation between transfer shaft (224) and cam follower ring (220); yet permit follower ring (220) to slide longitudinally along transfer shaft (224). As described in greater detail below, transfer shaft (224) may rotate about the longitudinal axis of transfer shaft (224) during operation of joint drive assembly (118); but transfer shaft (224) does not translate along the longitudinal axis of transfer shaft (224).

Figure 19:
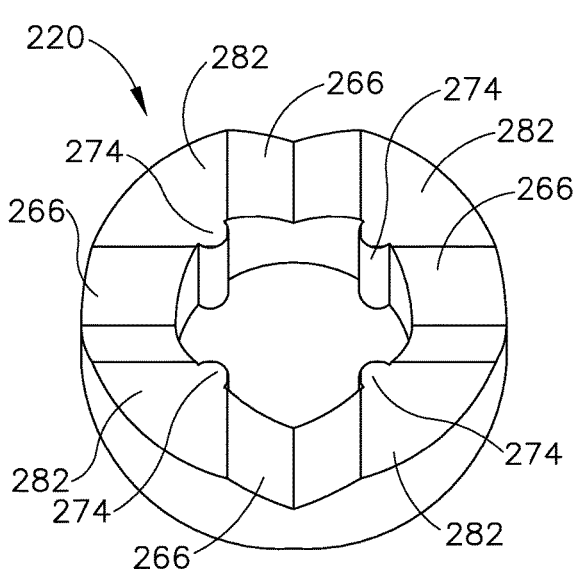
FIG. 19 depicts a top perspective view of a cam follower ring of the articulation control assembly of FIG. 14.
Figure 20:
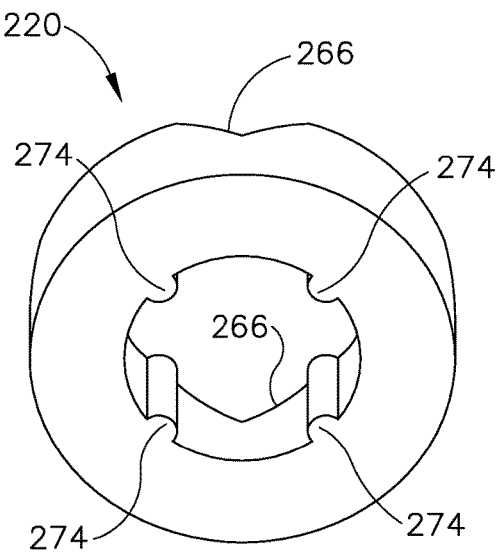
FIG. 20 depicts a bottom perspective view of the cam follower ring of FIG. 19.

With respect to FIGS. 19-20, cam follower ring (220) includes cam slots (266) that are configured to respectively receive cam studs (264) of rotary knob (214) (see FIG. 16). Cam follower ring (220) further includes a plurality of transversely extending ridges (274) that are configured to be respectively received within slots (272) (see FIG. 17). In other words, cam follower ring (220) is effectively splined onto lower portion (246) of transfer shaft (224) (see FIG. 17) such that cam follower ring (220) may translate relative to transfer shaft (224) (see FIG. 17) and rotary knob (214) (see FIG. 16); but cam follower ring (220) cannot rotate relative to transfer shaft (224) (see FIG. 17). While a variety of ridges and slots are described herein as being "transversely extending" in one example, it will be appreciated that such slots and ridges may be alternatively oriented so long as the cooperating slots and ridges are parallel with each other to provide for relative translation therebetween. As described in greater detail below, cam follower ring (220) may rotate about the longitudinal axis of transfer shaft (224) and simultaneously translate along the longitudinal axis of transfer shaft (224) during operation of joint drive assembly (118).

Figure 18:
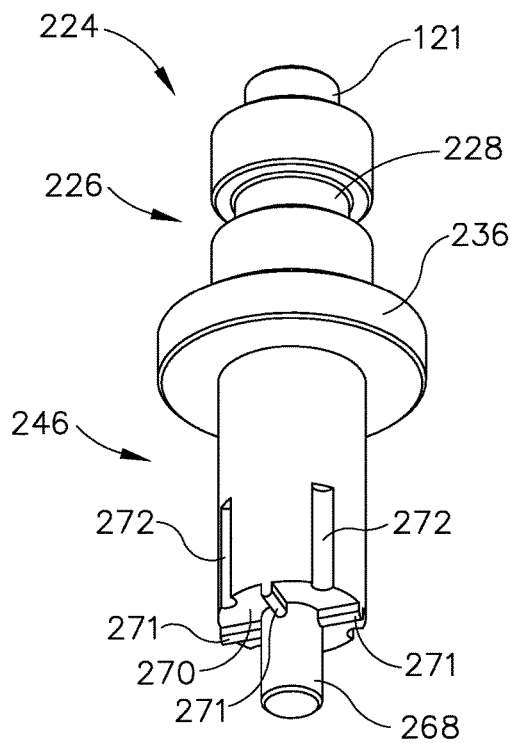
FIG. 18 depicts a bottom perspective view of the transfer shaft of FIG. 17.
Figure 21:
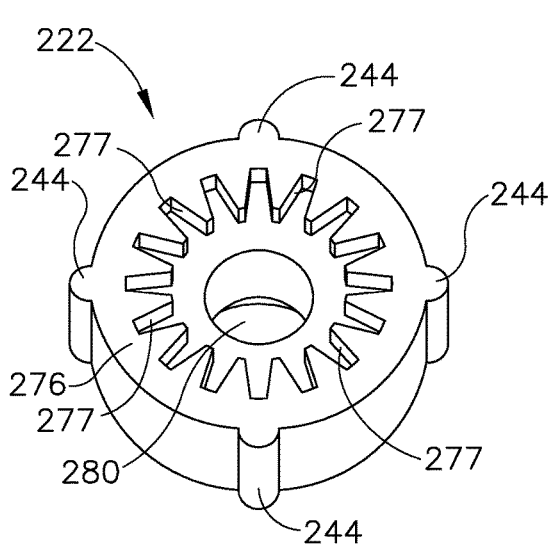
FIG. 21 depicts a top perspective view of a lock ring of the articulation control assembly of FIG. 14.
Figure 22:
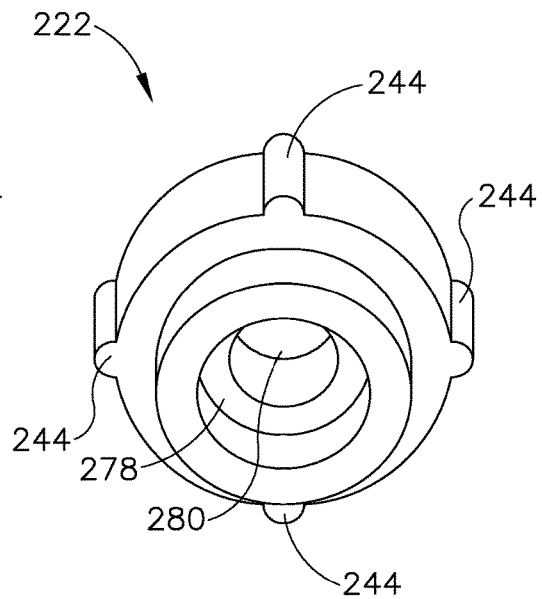
FIG. 22 depicts a bottom perspective view of the lock ring of FIG. 21.

As shown in FIGS. 21-22, lock ring (222) of the present example has an upper lock face (276) that is configured to engage lower lock face (270) of transfer shaft (224) (see FIG. 18). Lock ring (222) further includes a lower retainer seat (278) that is configured to capture biasing element (238) (see FIG. 14) against seat flange (234) of handle (211) (see FIG. 14). Upper lock face (276) further includes a plurality of lock slots (277) extending radially from the longitudinal axis of transfer shaft (224) and spaced angularly about upper lock face (276) to slidably receive lock tabs (271) (see FIG. 18), respectively. As discussed briefly above, lock ring (222) also has transversely extending ridges (244) that are slidably received within transversely extending slots (242) of housing (211) (see FIG. 14), such that lock ring (222) may translate (along the longitudinal axis of transfer shaft (224)) relative to housing (211) but not rotate relative to housing (211). Lock ring (222) also defines a lock bore (280) along the longitudinal axis of transfer shaft (224) to slidably receive lower extension (268) of transfer shaft (224) (see FIG. 18) to maintain coaxial alignment of lock ring (222) with transfer shaft (224) (see FIG. 18) in the locked and unlocked positions. As described in greater detail below, lock ring (222) may translate along the longitudinal axis of transfer shaft (224) during operation of joint drive assembly (118); but lock ring (222) does not rotate about the longitudinal axis of transfer shaft (224).

Figure 23:
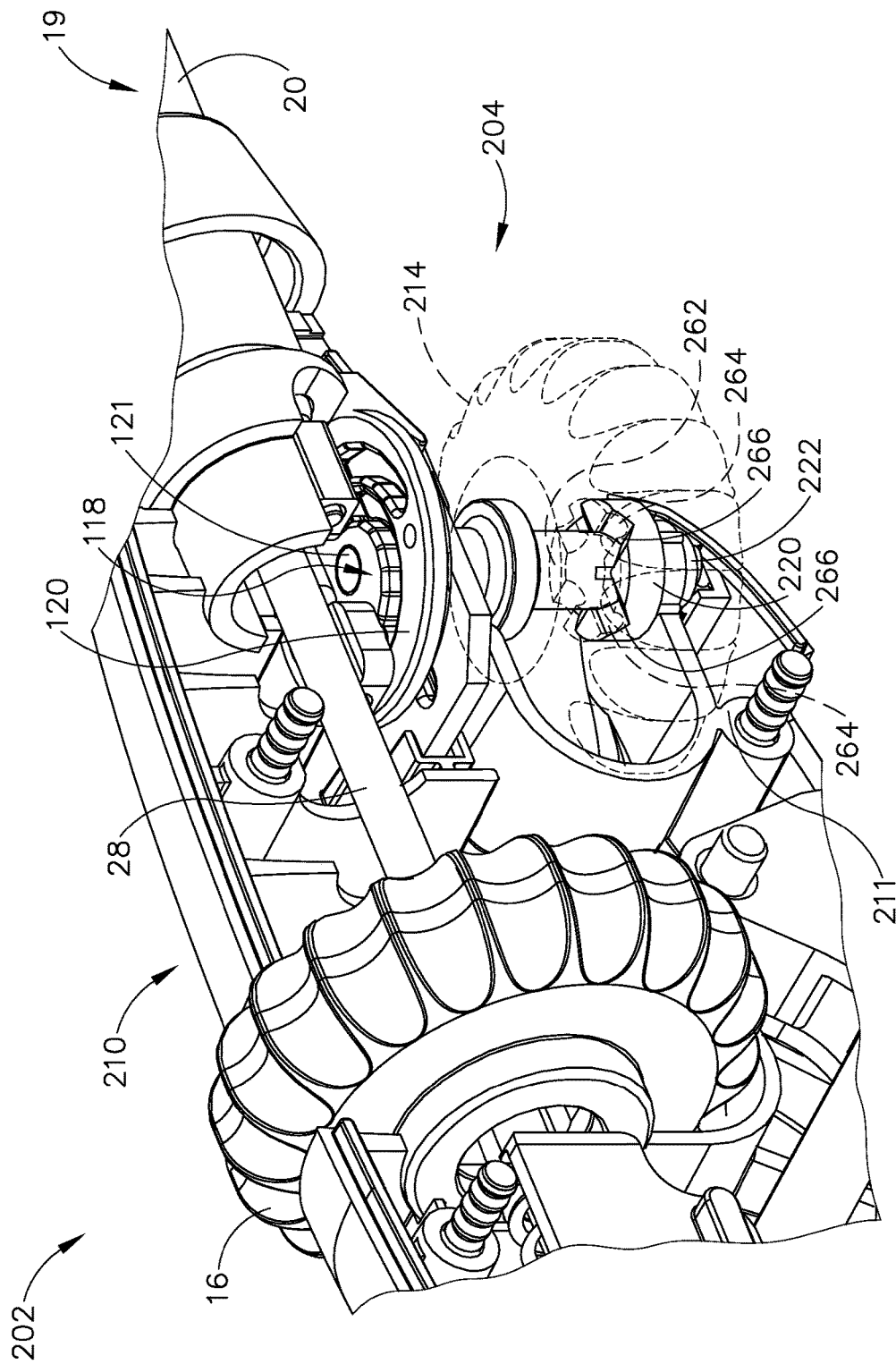
FIG. 23 depicts an enlarged rear perspective view of the articulation control assembly of FIG. 14, with various components removed for clarity.

With lock ring (222) biased upwardly in the locked position, clutch lock mechanism (204) is generally in the locked state shown in FIG. 23 when not being manipulated by the operator. In the locked state, upwardly biased lock ring (222) directs cam follower ring (220) upwardly against cam surface (262) of rotary knob (214). As such, cam studs (264) of rotary knob (214) are fully seated within corresponding cam slots (266) such that lock ring is in the upward, locked position. Specifically, upper lock face (276) (see FIG. 21) of lock ring (222) is engaged with lower lock face (270) (see FIG. 18) of transfer shaft (224). Thereby, receipt of lock tabs (271) (see FIG. 18) of transfer shaft (224) within corresponding lock slots (277) (see FIG. 21) of lock ring (222) fix the angular position of the transfer shaft (224) in one of a plurality of discrete, predetermined angular positions in cooperation with the relative positions of the lock slots (277) (see FIG. 21). In other words, the upwardly positioned lock ring (222) prevents rotation of transfer shaft (224) such that axle (121) of transfer shaft (224) seizes movement of joint drive assembly (118) and releasably locks articulation joint (23) (see FIG. 1) in a discrete, predetermined articulation position relative to the longitudinal axis (LA) of shaft (20).

In use, manipulation of rotary knob (214) transitions clutch lock mechanism (204) from the locked state to the unlocked state and then selectively positions articulation joint (23) (see FIG. 1) to another discrete, predetermined position along shaft (20) (see FIG. 1). FIGS. 24A-24H show an exemplary method of selectively positioning articulation joint (23) (see FIG. 1) from one discrete, predetermined articulation position to another discrete, predetermined articulation position. For purposes of clarity, movement of components will be described relative to upward, downward, left, and right directions as viewed in FIGS. 24A-24H. However, these directions are merely illustrative of the present drawings, and are not intended to limit potential manipulations and movement rotary knob (214) and clutch lock mechanism (204).

Figure 24A:
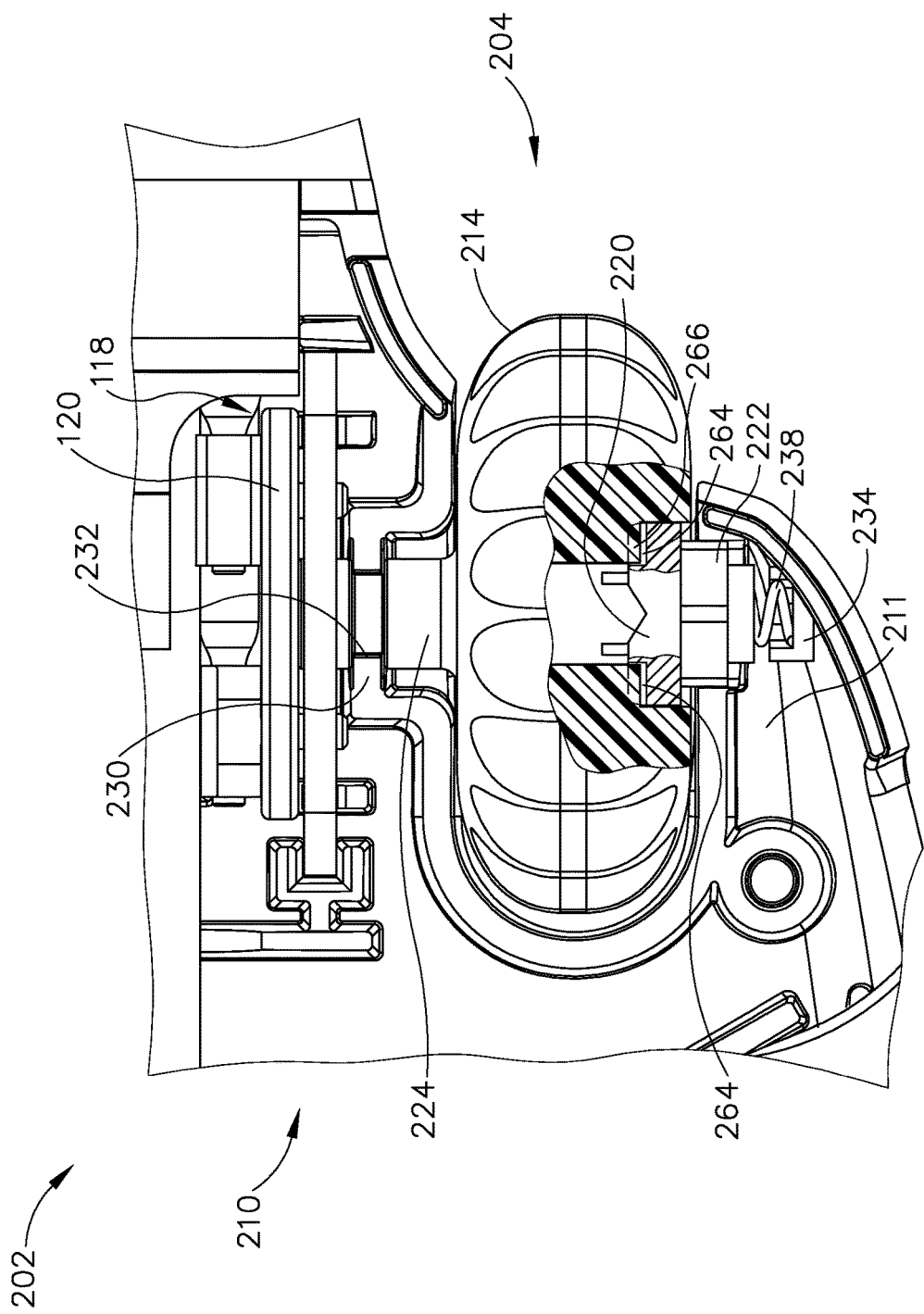
FIG. 24A depicts a side elevational view of the articulation control assembly of FIG. 14 in a locked state, with a portion of the rotary knob of FIG. 15 broken away in cross-section and with a portion of the cam follower ring of FIG. 19 broken away in cross section.

FIG. 24A shows clutch lock mechanism (204) in the locked state, seizing movement of joint drive assembly (118). In particular, lock ring (222) is in the upward position, engaging lock tabs (271) of transfer shaft (224) and thereby preventing any rotation of transfer shaft (224). Since transfer shaft (224) cannot rotate, disk (120) cannot rotate. Articulation joint (23) is thereby fully locked in its current state of articulation. To change the state of articulation of articulation joint (23), the operator user manipulates rotary knob (214) through a first partial rotation to the right, which may be referred to as counterclockwise to the operator looking down at a top view of surgical suturing instrument (202). Rotating rotary knob (214) the first partial rotation to the right as shown in FIG. 24B causes cam studs (264) of cam surface (262) to likewise rotate to the right.

Figure 24B:
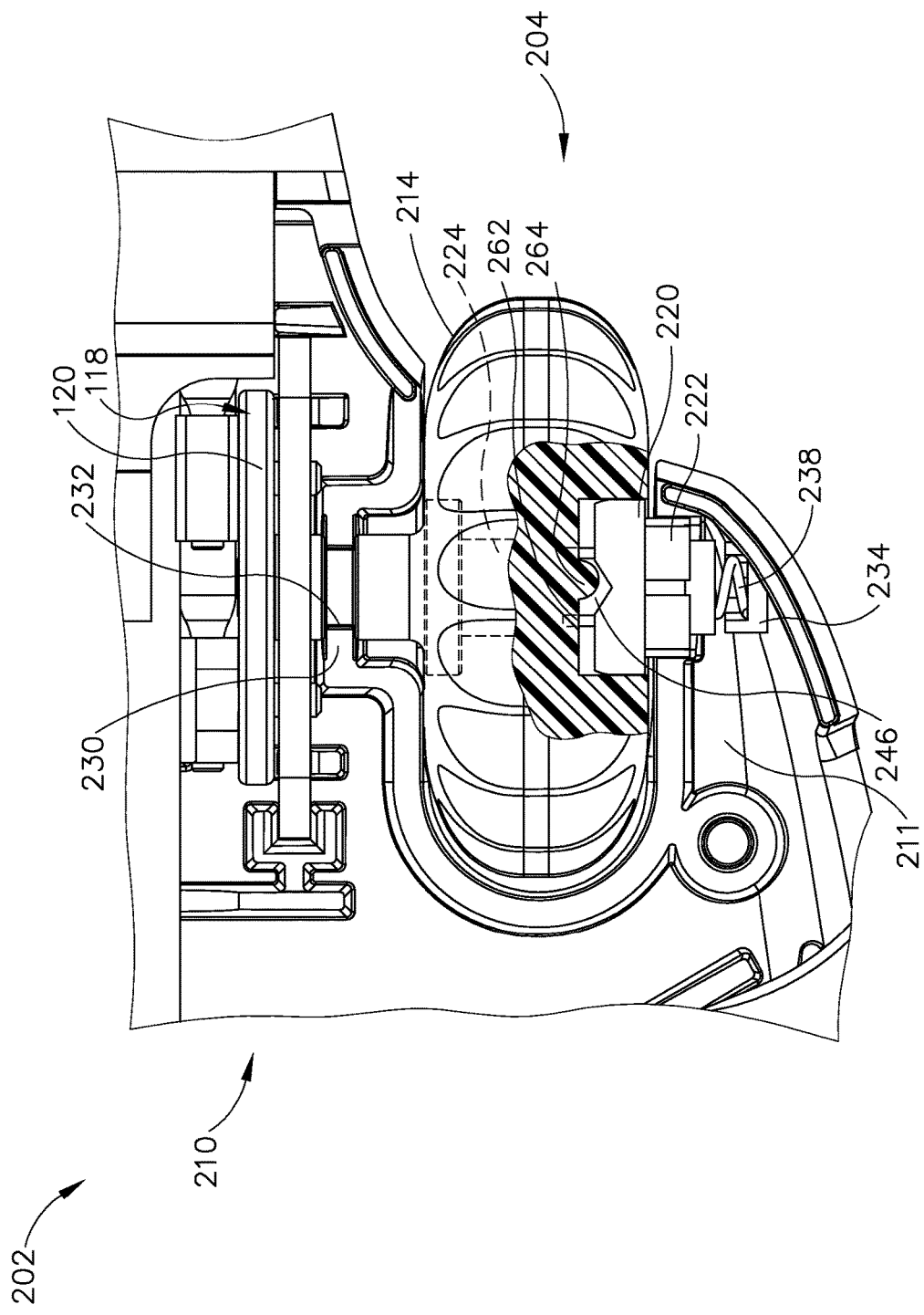
FIG. 24B depicts a side elevational view of the articulation control assembly of FIG. 14, with a portion of the rotary knob of FIG. 15 broken away in cross-section, and with rotation of the rotary knob depressing the lock ring from a locked position to an unlocked position.
Figure 24C:
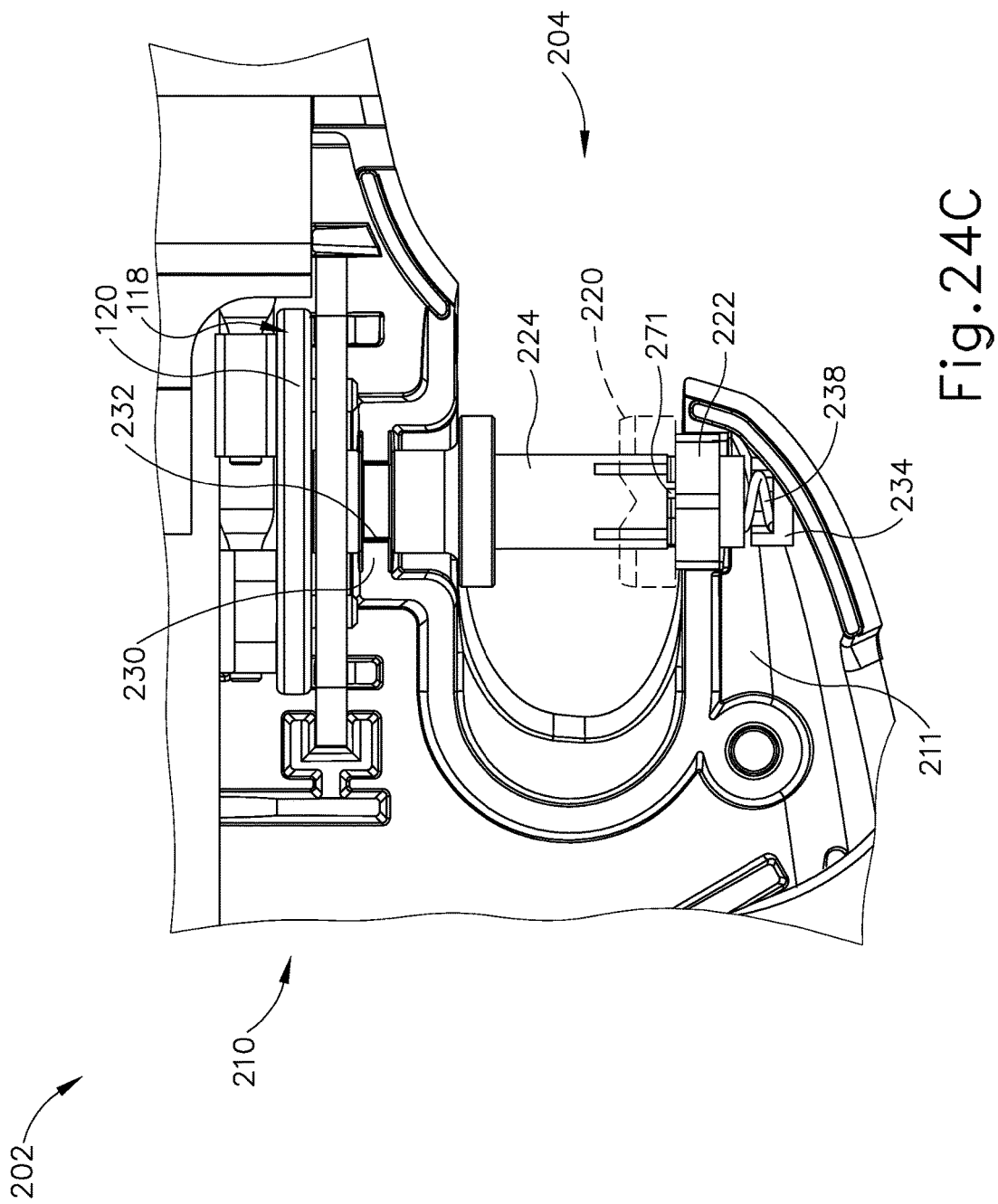
FIG. 24C depicts a side elevational view of the articulation control assembly of FIG. 14, with the rotary knob of FIG. 15 removed for clarity, and with the lock ring in the unlocked position such that the articulation assembly is in an unlocked state.
Figure 24D:
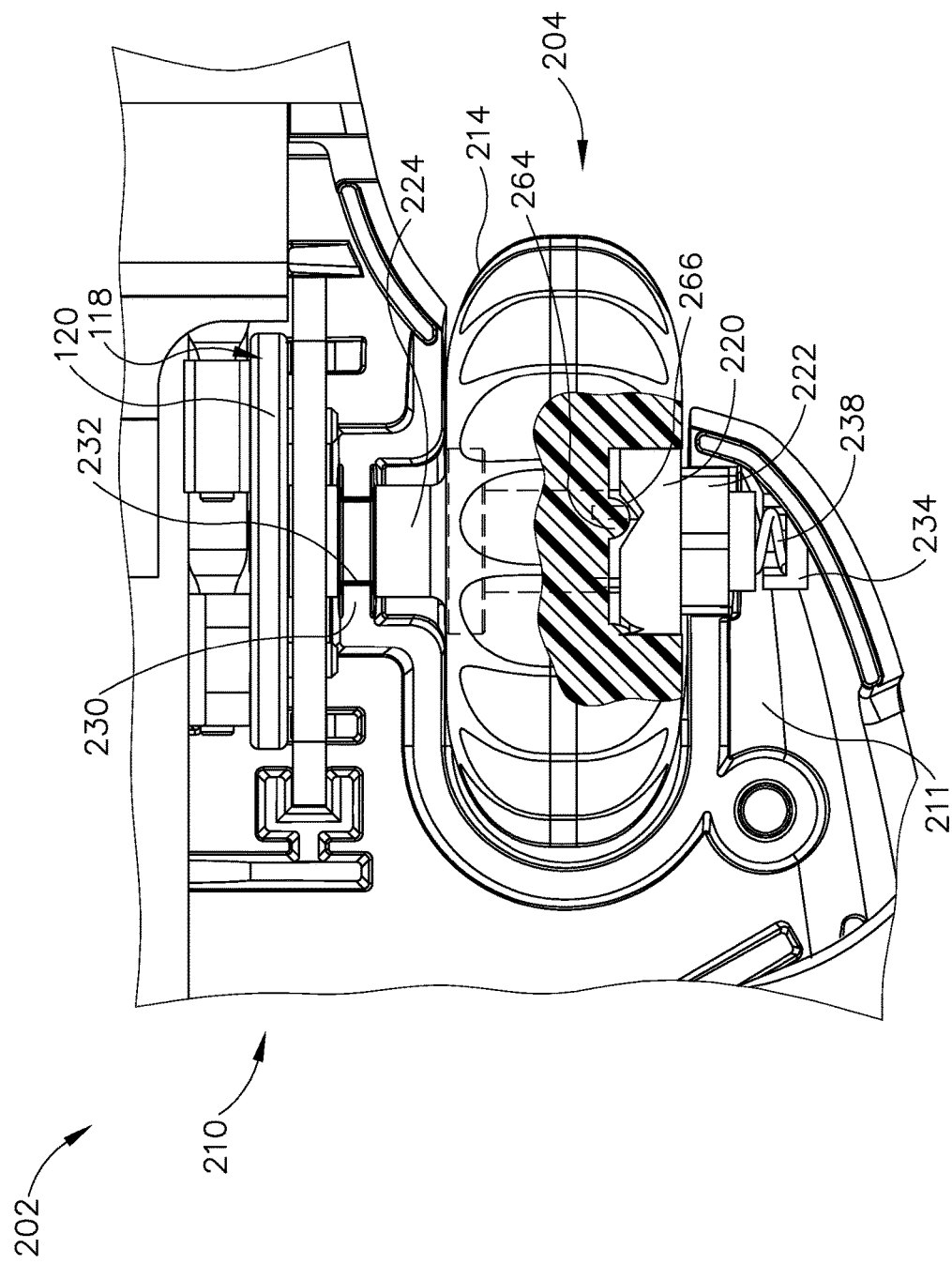
FIG. 24D depicts a side elevational view of the articulation control assembly of FIG. 14, with a portion of the rotary knob of FIG. 15 broken away in cross-section, and with continued rotation of the rotary knob in the unlocked state causing rotation of the transfer shaft via the cam follower ring mechanically coupled therebetween.

As rotary knob (214) rotates from the position shown in FIG. 24A to the position shown in FIG. 24B, cam studs (264) urge cam follower ring (220) downwardly along transfer shaft (224). As cam follower ring (220) translates downwardly along transfer shaft (224), cam follower ring (220) drives lock ring (222) downwardly. Lock ring (222) translates downwardly to eventually reach the unlocked position, as shown in FIG. 24C. In the unlocked position, lock slots (277) (see FIG. 21) of lock ring (222) release lock tabs (271) of transfer shaft (224) such that transfer shaft (224) and cam follower ring (220) are free to be rotatably driven together. To this end, at least a portion of cam studs (264) remain within cam slots (266) of cam follower ring (220), while biasing element (238) continues to provide an upward force holding cam follower ring (220) against rotary knob (214), as shown in FIG. 24D. Thereby, continued rotation of rotary knob (214) through second partial rotation to the right effectively drags transfer shaft (224) to the right via cam follower ring (220) engaged therebetween. Rotation of rotary knob (214) is thus transferred to disk (120) of joint drive assembly (118) to articulate articulation joint (23) (see FIG. 1). The operator continues to rotate rotary knob (114) until articulation joint (23) is positioned in another discrete, predetermined position as selected by the user.

It should be understood that, despite the partial rotation of rotary knob (214) during the transition from the state shown in FIG. 24A to the state shown in FIGS. 24B and 24C, transfer shaft (224) does not rotate during the transition from the state shown in FIG. 24A to the state shown in FIGS. 24B and 24C. The operator will thus rotate rotary knob (214) through a first range of angular motion to unlock clutch lock mechanism (204) without any corresponding articulation movement occurring at articulation joint (23). However, as the operator continues to rotate rotary knob (214) through a second range of angular motion (e.g., from the state shown in FIGS. 24B and 24C to the state shown in FIG. 24D), the rotation of rotary knob (214) will result in corresponding articulation movement at articulation joint (23).

Figure 24F:
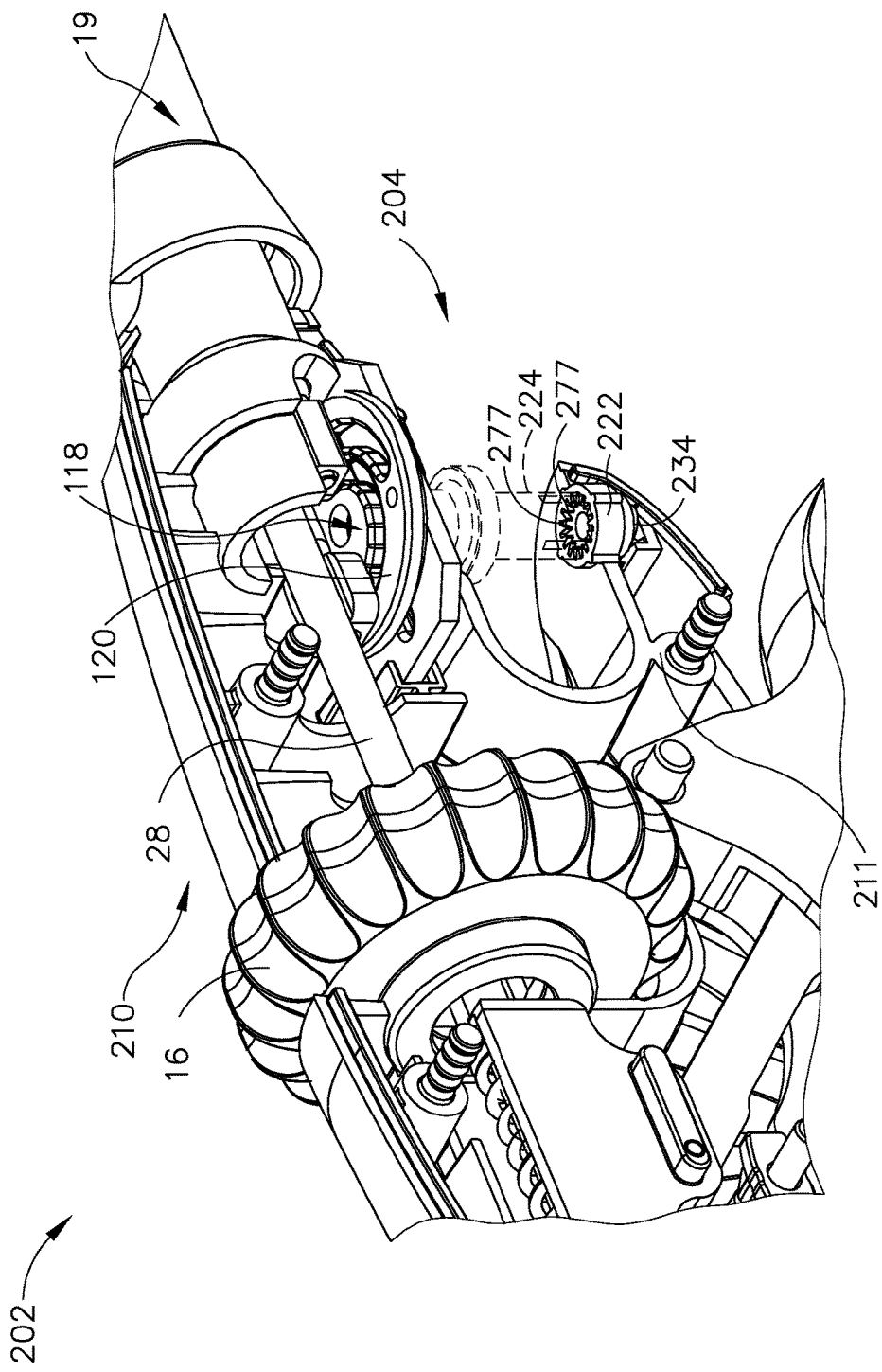
FIG. 24F depicts an enlarged rear perspective view of the articulation control assembly of FIG. 14, with the rotary knob of FIG. 15 removed for clarity, with the lock ring released to the locked position against the transfer shaft after the desirable rotation of the rotary knob and the cam follower ring.

Upon ceasing rotation of rotary knob (214), lock tabs (271) align with other respective lock slots (277) as shown in FIGS. 24E-24F. In addition, without the downward force generated by rotating cam studs (264) (see FIG. 24D) within cam slots (266) against cam follower ring (220), biasing element (238) directs lock ring (222) upwardly into the locked position for engagement with transfer shaft (224). FIGS. 24F-24G show lock ring (222) in the locked position such that clutch lock mechanism (204) has returned to the locked state.

Figure 24H:
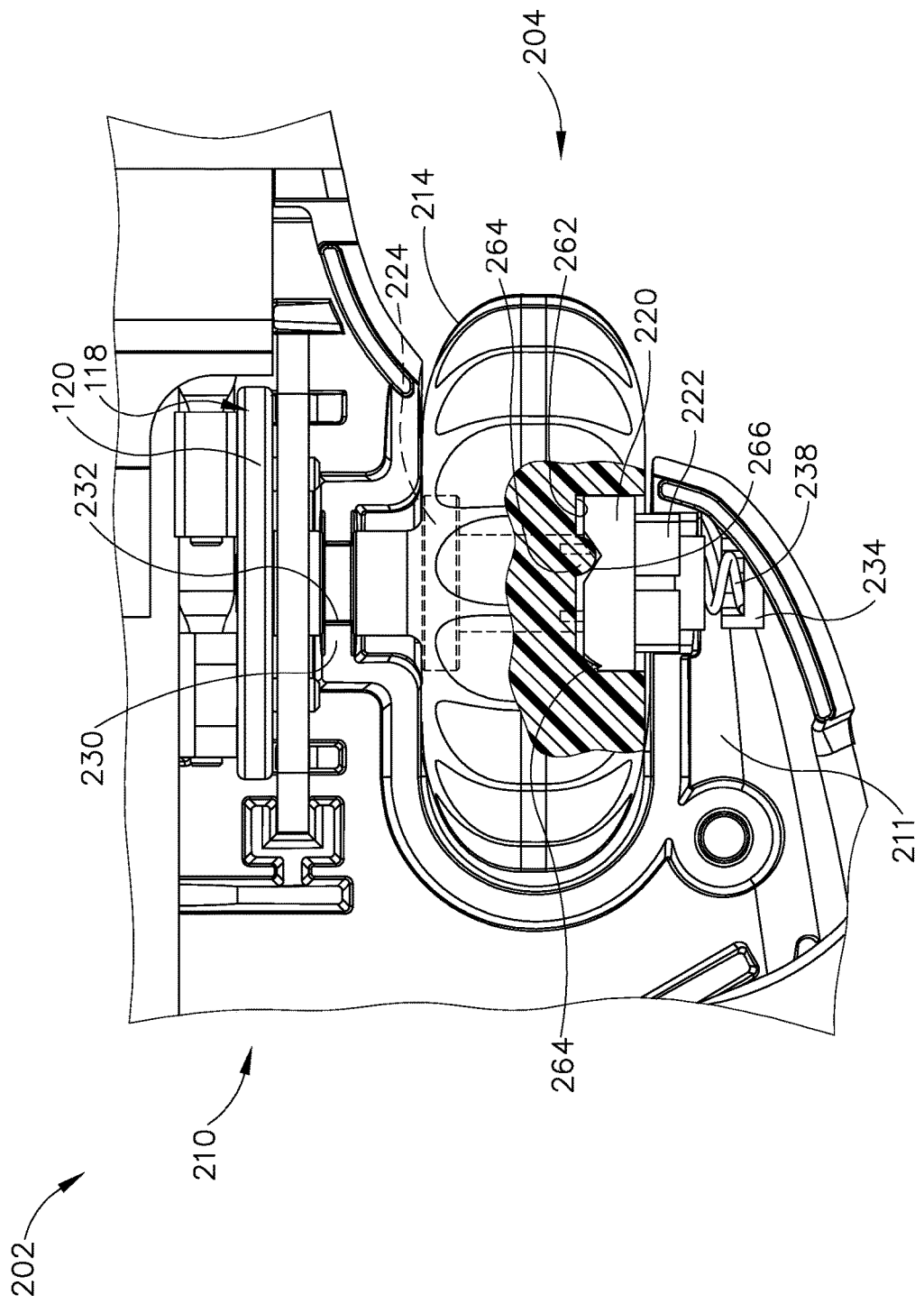
FIG. 24H depicts a side elevational view of the articulation control assembly of FIG. 14, with a portion of the rotary knob of FIG. 15 broken away in cross-section, and with the articulation assembly in the locked state after the desirable rotation of the rotary knob.

Similarly, as shown in FIG. 24H, cam follower ring (220) is again sandwiched between cam surface (262) of rotary knob (214) and lock ring (222) such that cam studs (264) are fully received within cam slots (266). Clutch lock mechanism (204) returned to the locked state thereby seizes joint drive assembly (118) for locking articulation joint (23) (see FIG. 1) in another discrete, predetermined position and inhibits inadvertently repositioning articulation joint (23) (see FIG. 1) unless the user selectively manipulates rotary knob (214). Clutch lock mechanism (204) will thus prevent backlash in response to laterally oriented forces exerted against cartridge (30), cartridge receiving assembly (50), or other regions of distal end portion (22) of shaft (20) distal to articulation joint (23).

While the above description positions transfer shaft (224) and, in turn, articulation joint (23) (see FIG. 1) in discrete, predetermined articulation positions via the plurality of lock slots (277) shown and described herein, it will be appreciated that more or fewer lock slots (277) may be used for more or less discrete positions, respectively. Similarly, lock slots (277) may be alternatively positioned to alter particular discrete positions from those shown in the present example. Furthermore, it will be appreciated that another example may use an alternative structure to lock slots (277) such that any desirable position selected by the user may be chosen to lock articulation joint (23) (see FIG. 1). For instance, lock slots (277) may be substituted with a surface providing a high coefficient of friction, such that articulation joint (23) and joint drive assembly (118) are effectively locked through frictional braking at a virtually infinite number of articulation positions within the full articulation range of articulation joint (23).

As discussed above, cam studs (264) generally remain within cam slots (266) in order to drag cam follower ring (220) and transfer shaft (224) to the right as shown in FIG. 24D. Alternatively, in the event that the operator attempts to turn rotary knob (214) while distal end portion (22) of shaft (20) (see FIG. 1) is captured against an object, such as patient tissue or surgical equipment, clutch lock mechanism (204) will slip to order to inhibit a greater torque from potentially damaging one or more portions of surgical suturing instrument (202). More particularly, additional torque will cause cam studs (264) to direct cam follower ring (220) further downwardly from the position shown in FIG. 24D until cam studs (264) rise out of cam slots (266) onto a planar cam surface (282). Rotary knob (214) will then be free to rotate independently of the remainder of clutch lock mechanism (204) until cam studs (264) are again received within cam slots (266) and returned to the locked state. Furthermore, the movement of cam studs (264) in and out of cam slots (266) will provide tactile feedback to the user in order to indicate that distal end portion (22) of shaft (20) (see FIG. 1) is captured against the object. The operator may then reposition the shaft (20) (see FIG. 1) and again attempt to articulate articulation joint (23) (see FIG. 1) as needed.

While the above descriptions refer to rightward (i.e., counterclockwise) rotation, it will be appreciated that leftward (i.e., clockwise) rotation is also contemplated for positioning and locking articulation joint (23) of FIG. 1. It will be appreciated that the above description will effectively occur in the opposite directions to those discussed above in the event of leftward (i.e., clockwise) rotation. Thus, the description of rightward (i.e., counterclockwise) rotation is merely exemplary and not intended to limit the invention to the particular rotation described herein.

In some versions of surgical suturing instrument (202), shaft assembly (19) and/or handle assembly (210) may be provided as being disposable or reusable. Versions with reusable components are intended to be cleaned, sterilized, and reused for multiple surgical procedures, and may include a flush port (not shown) to facilitate cleaning. In some such versions, the preferable life cycle of a reusable instrument may be at least 50 operations, more particularly at least 150 operations, or more particularly at least 200 operations. Reusable components may be built using materials that can withstand autoclave sterilization temperatures of at least 135 degrees Celsius, although low temperature materials can also be used with low temperature sterilization techniques known in the art.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument for treating a patient, comprising: (a) a shaft assembly, comprising: (i) a proximal end portion, (ii) a distal end portion, wherein the distal end portion is configured to treat tissue, and (iii) an articulation joint, wherein the articulation joint is operable to selectively articulate the distal end portion relative to the proximal end portion; (b) a body assembly, wherein the shaft assembly extends distally from the body assembly, wherein the body assembly comprises: (i) a joint drive assembly operatively connected to the articulation joint and configured to actuate the articulation to thereby articulate the distal end portion relative to the proximal end portion, (ii) an actuator, and (iii) a clutch lock mechanism operatively connected between the actuator and the joint drive assembly, wherein the actuator is configured to actuate the clutch lock mechanism from a locked state to an unlocked state upon selective movement of the actuator, wherein the clutch lock mechanism in the locked state is configured to seize the joint drive assembly and thereby inhibit movement at the articulation joint, and wherein the clutch lock mechanism in the unlocked state is configured to transmit movement of the actuator to the joint drive assembly and thereby drive articulation of the distal end portion relative to the proximal end portion.

EXAMPLE 2

The surgical instrument of claim 1, wherein the clutch lock mechanism in the lock state is configured to seize the joint drive assembly in one of a plurality of discrete positions, and wherein the clutch lock mechanism in the unlocked state is configured to transmit movement of the actuator to the joint drive assembly and move the joint drive assembly toward another one of the plurality of discrete positions.

EXAMPLE 3

The surgical instrument of claim 1, wherein the actuator comprises a rotary knob configured to selectively rotate about an axis, wherein the clutch lock mechanism further includes: (A) a transfer shaft operatively connected between the rotary knob and the joint drive assembly and configured to rotate about the axis, and (B) a lock member resiliently mounted toward the transfer shaft and moveable between a locked position and an unlocked position, wherein the lock member in the locked position engages the transfer shaft and is thereby configured to inhibit movement of the transfer shaft for seizing the joint drive assembly, and wherein the lock member in the unlocked position is configured to disengage from the transfer shaft such that rotation of the rotary knob is configured to rotate the transfer shaft for transmitting movement of the rotary knob to the joint drive assembly.

EXAMPLE 4

The surgical instrument of claim 3, wherein the body assembly further includes a housing and the lock member is resiliently mounted to the housing and interlocked therewith to prevent relative rotation therebetween while the lock member translates between the locked and unlocked positions.

EXAMPLE 5

The surgical instrument of claim 4, wherein the lock member defines a plurality of lock slots, wherein the transfer shaft includes at least one tab, and in the locked position at least one of the plurality of lock slots receives the at least one tab such that the lock member is engaged within the transfer shaft.

EXAMPLE 6

The surgical instrument of claim 5, wherein the lock member is in the form of a lock ring having an upper surface, wherein the plurality of lock slots are arranged about the upper surface, and wherein the at least one tab of the transfer shaft extends downwardly from the transfer shaft toward the lock ring for engagement therewith.

EXAMPLE 7

The surgical instrument of claim 6, wherein the transfer shaft has a lower portion and an upper portion, wherein the lower portion of the transfer shaft includes the at least one tab, and wherein the upper portion of the transfer shaft is secured to the joint drive assembly.

EXAMPLE 8

The surgical instrument of claim 3, wherein the rotary knob includes a cam surface, wherein the clutch lock mechanism further includes a cam follower splined onto the transfer shaft such that the cam follower is configured to translate along the axis relative to the transfer shaft and inhibit relative rotation between the cam follower and the transfer shaft about the axis, wherein the cam follower is received against the cam surface of the rotary knob such that rotating the rotary knob will drive the cam follower downwardly against the lock member and, in turn, drive the lock member downwardly along the axis toward the unlocked positioned for disengaging the lock member from the transfer shaft.

EXAMPLE 9

The surgical instrument of claim 8, wherein the rotary knob and the lock member are configured such that further rotation of the rotary knob with the lock member in the unlocked position will rotate the cam follower and, in turn, rotate the transfer shaft splined thereto in order to transmit rotation of the rotary knob to the joint drive assembly.

EXAMPLE 10

The surgical instrument of claim 9, wherein the cam follower is in the form of a cam follower ring having a bore extending therethrough along the axis, and the bore receives a lower portion of the transfer shaft.

EXAMPLE 11

The surgical instrument of claim 10, wherein the transfer shaft has an upper portion opposite the lower portion, wherein the upper portion of the transfer shaft is secured to the joint drive assembly.

EXAMPLE 12

The surgical instrument of claim 1, wherein the actuator comprises a rotary knob configured to selectively rotate about an axis, wherein the clutch lock mechanism further includes: (A) a transfer shaft operatively connected between the rotary knob and the joint drive assembly and configured to rotate about the axis, and (B) a cam follower splined onto the transfer shaft such that the cam follower is configured to inhibit relative rotation between the cam follower and the transfer shaft about the axis, wherein the cam follower received against the cam surface of the rotary knob such that rotating the rotary knob with the clutch lock mechanism in the unlocked state will rotate the cam follower and, in turn, rotate the transfer shaft splined thereto in order to transmit rotation of the rotary knob to the joint drive assembly.

EXAMPLE 13

The surgical instrument of claim 12, wherein the cam follower is in the form of a cam follower ring having a bore extending therethrough along the axis, wherein the bore receives a lower portion of the transfer shaft.

EXAMPLE 14

The surgical instrument of claim 13, wherein the transfer shaft has an upper portion opposite the lower portion, wherein the upper portion of the transfer shaft is secured to the joint drive assembly.

EXAMPLE 15

The surgical instrument of claim 1, wherein the actuator comprises a rotary knob configured to selectively rotate about an axis, wherein the clutch lock mechanism further includes: (A) a transfer shaft having an upper portion and a lower portion, wherein the transfer shaft is configured to rotate about the axis, wherein the upper portion is secured to the joint drive assembly, wherein the rotary knob has a hole extending therethrough along the axis, the hole receiving a lower portion of the transfer shaft, wherein the lower portion of the transfer shaft is operatively connected to the rotary knob such that rotating the lower portion of the transfer shaft via the rotary knob will rotate the upper portion of the transfer shaft for directing the joint drive assembly to articulate the articulation joint, and (B) a cam member connecting the rotary knob to the transfer shaft such that the rotary knob is configured to move relative to the transfer shaft.

EXAMPLE 16

A surgical instrument for treating a patient, comprising: (a) a joint drive assembly configured to connect to an articulation joint of a shaft assembly for articulating the articulation joint; (b) an actuator; and (c) a clutch lock mechanism operatively connected between the actuator and the joint drive assembly, wherein the actuator is configured to actuate the clutch lock mechanism from a locked state to an unlocked state upon selective movement of the actuator, wherein the clutch lock mechanism in the locked state is configured to seize the joint drive assembly for inhibiting movement of the articulation joint, and wherein the clutch lock mechanism in the unlocked state is configured to transmit movement of the actuator to the joint drive assembly for selectively articulating the articulation joint for accessing a tissue within the patient.

EXAMPLE 17

A method of articulating a portion of a shaft assembly with a body assembly having joint drive assembly, an actuator, and a clutch lock mechanism, the clutch lock mechanism operatively connected between the joint drive assembly and the actuator and configured to actuate between a lock state and an unlocked state, the method comprising: (a) seizing movement of the joint drive assembly in order to inhibit articulation of the portion of the shaft assembly with the clutch lock mechanism in the locked state; (b) selectively moving the actuator through a first range of motion and thereby actuating the joint drive assembly to the unlocked state; (c) selectively moving the actuator through a second range of motion, with clutch lock mechanism in the unlocked state, thereby directing the joint drive assembly to move and articulate the portion of the shaft assembly; and (d) selectively ceasing movement of the actuator thereby actuating the joint drive assembly to the locked state.

EXAMPLE 18

The method of claim 17, wherein the clutch lock mechanism includes a transfer shaft and a lock member, wherein the act of seizing movement of the joint drive assembly further includes engaging the lock member against the transfer shaft in a locked position in order to inhibit movement of the transfer shaft such that the clutch lock mechanism is in the locked state.

EXAMPLE 19

The method of claim 17, wherein the actuator comprises a rotary knob configured to selectively rotate about an axis, wherein the clutch lock mechanism includes a transfer shaft and a lock member, wherein the act of selectively moving the actuator through a first range of motion and thereby actuating the joint drive assembly to the unlocked state further includes: (a) rotating the rotary knob and directing the rotary member against the lock member; and (b) driving the lock member with the rotary knob from a locked position to the unlocked position to disengage the lock member from the transfer shaft.

EXAMPLE 20

The method of claim 17, wherein the actuator comprises a rotary knob configured to selectively rotate about an axis, wherein the clutch lock mechanism includes a transfer shaft and a cam follower, wherein the act of selectively moving the actuator through a second range of motion, with clutch lock mechanism in the unlocked state, thereby directing the joint drive assembly to move and articulate the portion of the shaft assembly further includes: (a) rotating the rotary knob and directing the rotary member against the cam member in order to rotate the cam member; and (b) directing the cam member against the transfer shaft in order to rotate the transfer shaft.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument for treating a patient, comprising:
   (a) a shaft assembly, comprising:
      (i) a proximal end portion,
      (ii) a distal end portion, wherein the distal end portion is configured to treat tissue, and
      (iii) an articulation joint, wherein the articulation joint is operable to selectively articulate the distal end portion relative to the proximal end portion;
   (b) a body assembly, wherein the shaft assembly extends distally from the body assembly, wherein the body assembly comprises:
      (i) a joint drive assembly operatively connected to the articulation joint and configured to actuate the articulation to thereby articulate the distal end portion relative to the proximal end portion,
      (ii) an actuator, wherein the actuator comprises a rotary knob configured to selectively rotate about an axis, and
      (iii) a clutch lock mechanism operatively connected between the actuator and the joint drive assembly, wherein the actuator is configured to actuate the clutch lock mechanism from a locked state to an unlocked state upon selective movement of the actuator, wherein the clutch lock mechanism in the locked state is configured to seize the joint drive assembly and thereby inhibit movement at the articulation joint, and wherein the clutch lock mechanism in the unlocked state is configured to transmit movement of the actuator to the joint drive assembly and thereby drive articulation of the distal end portion relative to the proximal end portion, wherein the clutch lock mechanism further includes:
         (A) a transfer shaft operatively connected between the rotary knob and the joint drive assembly and configured to rotate about the axis, and
         (B) a lock member resiliently mounted toward the transfer shaft and moveable between a locked position and an unlocked position, wherein the lock member in the locked position engages the transfer shaft and is thereby configured to inhibit movement of the transfer shaft for seizing the joint drive assembly, and wherein the lock member in the unlocked position is configured to disengage from the transfer shaft such that rotation of the rotary knob is configured to rotate the transfer shaft for transmitting movement of the rotary knob to the joint drive assembly.

2. The surgical instrument of claim 1, wherein the clutch lock mechanism in the lock state is configured to seize the joint drive assembly in one of a plurality of discrete positions, and wherein the clutch lock mechanism in the unlocked state is configured to transmit movement of the actuator to the joint drive assembly and move the joint drive assembly toward another one of the plurality of discrete positions.

3. The surgical instrument of claim 1, wherein the body assembly further includes a housing and the lock member is resiliently mounted to the housing and interlocked therewith to prevent relative rotation therebetween while the lock member translates between the locked and unlocked positions.

4. The surgical instrument of claim 3, wherein the lock member defines a plurality of lock slots, wherein the transfer shaft includes at least one tab, and in the locked position at least one of the plurality of lock slots receives the at least one tab such that the lock member is engaged within the transfer shaft.

5. The surgical instrument of claim 4, wherein the lock member is in the form of a lock ring having an upper surface, wherein the plurality of lock slots are arranged about the upper surface, and wherein the at least one tab of the transfer shaft extends downwardly from the transfer shaft toward the lock ring for engagement therewith.

6. The surgical instrument of claim 5, wherein the transfer shaft has a lower portion and an upper portion, wherein the lower portion of the transfer shaft includes the at least one tab, and wherein the upper portion of the transfer shaft is secured to the joint drive assembly.

7. The surgical instrument of claim 1, wherein the rotary knob includes a cam surface, wherein the clutch lock mechanism further includes a cam follower splined onto the transfer shaft such that the cam follower is configured to translate along the axis relative to the transfer shaft and inhibit relative rotation between the cam follower and the transfer shaft about the axis, wherein the cam follower is received against the cam surface of the rotary knob such that rotating the rotary knob will drive the cam follower downwardly against the lock member and, in turn, drive the lock member downwardly along the axis toward the unlocked positioned for disengaging the lock member from the transfer shaft.

8. The surgical instrument of claim 7, wherein the rotary knob and the lock member are configured such that further rotation of the rotary knob with the lock member in the unlocked position will rotate the cam follower and, in turn, rotate the transfer shaft splined thereto in order to transmit rotation of the rotary knob to the joint drive assembly.

9. The surgical instrument of claim 8, wherein the cam follower is in the form of a cam follower ring having a bore extending therethrough along the axis, and the bore receives a lower portion of the transfer shaft.

10. The surgical instrument of claim 9, wherein the transfer shaft has an upper portion opposite the lower portion, wherein the upper portion of the transfer shaft is secured to the joint drive assembly.

11. The surgical instrument of claim 1, wherein the rotary knob is configured to rotate in a plane that is spaced below and generally parallel with the shaft assembly.

12. The surgical instrument of claim 1, wherein the joint drive assembly includes a disk, and wherein the transfer shaft includes an axle that connects the rotary knob to the disk that also rotates in a plane generally parallel with the transfer shaft.

13. The surgical instrument of claim 1, wherein the rotary knob is not co-axial with the shaft assembly.

14. The surgical instrument of claim 1, wherein the axis extends generally perpendicular to a longitudinal axis of the shaft assembly.

15. A surgical instrument for treating a patient, comprising:
(a) a shaft assembly, comprising:
(i) a proximal end portion,
(ii) a distal end portion, wherein the distal end portion is configured to treat tissue, and
(iii) an articulation joint, wherein the articulation joint is operable to selectively articulate the distal end portion relative to the proximal end portion;
(b) a body assembly, wherein the shaft assembly extends distally from the body assembly, wherein the body assembly comprises:
(i) a joint drive assembly operatively connected to the articulation joint and configured to actuate the articulation to thereby articulate the distal end portion relative to the proximal end portion,
(ii) an actuator, wherein the actuator comprises a rotary knob configured to selectively rotate about an axis, and
(iii) a clutch lock mechanism operatively connected between the actuator and the joint drive assembly, wherein the actuator is configured to actuate the clutch lock mechanism from a locked state to an unlocked state upon selective movement of the actuator, wherein the clutch lock mechanism in the locked state is configured to seize the joint drive assembly and thereby inhibit movement at the articulation joint, and wherein the clutch lock mechanism in the unlocked state is configured to transmit movement of the actuator to the joint drive assembly and thereby drive articulation of the distal end portion relative to the proximal end portion, wherein the clutch lock mechanism further includes:
(A) a transfer shaft operatively connected between the rotary knob and the joint drive assembly and configured to rotate about the axis, and
(B) a cam follower splined onto the transfer shaft such that the cam follower is configured to inhibit relative rotation between the cam follower and the transfer shaft about the axis, wherein the cam follower is received against the cam surface of the rotary knob such that rotating the rotary knob with the clutch lock mechanism in the unlocked state will rotate the cam follower and, in turn, rotate the transfer shaft splined thereto in order to transmit rotation of the rotary knob to the joint drive assembly.

16. The surgical instrument of claim 15, wherein the cam follower is in the form of a cam follower ring having a bore extending therethrough along the axis, wherein the bore receives a lower portion of the transfer shaft.

17. The surgical instrument of claim 16, wherein the transfer shaft has an upper portion opposite the lower portion, wherein the upper portion of the transfer shaft is secured to the joint drive assembly.

18. The surgical instrument of claim 15, wherein the axis extends generally perpendicular to a longitudinal axis of the shaft assembly.

19. A surgical instrument for treating a patient, comprising:
(a) a shaft assembly, comprising:
(i) a proximal end portion,
(ii) a distal end portion, wherein the distal end portion is configured to treat tissue, and
(iii) an articulation joint, wherein the articulation joint is operable to selectively articulate the distal end portion relative to the proximal end portion;
(b) a body assembly, wherein the shaft assembly extends distally from the body assembly, wherein the body assembly comprises:
(i) a joint drive assembly operatively connected to the articulation joint and configured to actuate the articulation to thereby articulate the distal end portion relative to the proximal end portion,
(ii) an actuator, wherein the actuator comprises a rotary knob configured to selectively rotate about an axis, and
(iii) a clutch lock mechanism operatively connected between the actuator and the joint drive assembly, wherein the actuator is configured to actuate the clutch lock mechanism from a locked state to an unlocked state upon selective movement of the actuator, wherein the clutch lock mechanism in the locked state is configured to seize the joint drive assembly and thereby inhibit movement at the articulation joint, and wherein the clutch lock mechanism in the unlocked state is configured to transmit movement of the actuator to the joint drive assembly and thereby drive articulation of the distal end portion relative to the proximal end portion, wherein the clutch lock mechanism further includes:

(A) a transfer shaft having an upper portion and a lower portion, wherein the transfer shaft is configured to rotate about the axis, wherein the upper portion is secured to the joint drive assembly, wherein the rotary knob has a hole extending therethrough along the axis, the hole receiving a lower portion of the transfer shaft, wherein the lower portion of the transfer shaft is operatively connected to the rotary knob such that rotating the lower portion of the transfer shaft via the rotary knob will rotate the upper portion of the transfer shaft for directing the joint drive assembly to articulate the articulation joint, and (B) a cam member connecting the rotary knob to the transfer shaft such that the rotary knob is configured to move relative to the transfer shaft.

20. The surgical instrument of claim 19, wherein the axis extends generally perpendicular to a longitudinal axis of the shaft assembly.

* * * * *